(12) United States Patent
Yun et al.

(10) Patent No.: US 11,045,140 B2
(45) Date of Patent: *Jun. 29, 2021

(54) HOMEOSTATIC CAPACITY EVALUATION

(71) Applicant: Palo Alto Investors, Palo Alto, CA (US)

(72) Inventors: Anthony Joonkyoo Yun, Menlo Park, CA (US); Conrad Minkyoo Yun, San Mateo, CA (US)

(73) Assignee: Palo Alto Investors, Palo Alto, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/996,160

(22) Filed: Jun. 1, 2018

(65) Prior Publication Data

US 2018/0271440 A1 Sep. 27, 2018

Related U.S. Application Data

(63) Continuation-in-part of application No. 15/061,645, filed on Mar. 4, 2016, now Pat. No. 10,631,781.

(Continued)

(51) Int. Cl.
*A61B 5/02* (2006.01)
*A61B 5/00* (2006.01)
(Continued)

(52) U.S. Cl.
CPC .......... *A61B 5/4884* (2013.01); *A61B 5/0205* (2013.01); *A61B 5/4848* (2013.01);
(Continued)

(58) Field of Classification Search
CPC ... A61B 5/02405; A61B 5/165; A61B 5/4035; A61B 5/4848; A61B 5/7275;
(Continued)

(56) References Cited

U.S. PATENT DOCUMENTS 7,020,521 B1 3/2006 Brewer et al.
7,149,574 B2 12/2006 Yun et al.
(Continued)

FOREIGN PATENT DOCUMENTS

JP 2000-262480 A 9/2000
KR 10-131528 B1 10/2013

OTHER PUBLICATIONS

Russoniello et al. "Heart Rate Variablity and Biological Age: Implications for Health and Gamine." Cyberpsychology, Behavior and Social Networking, vol. 16, No. 4, pp. 302-308. (Year: 2013).*
(Continued)

*Primary Examiner* — Eric D. Bertram
(74) *Attorney, Agent, or Firm* — Peter W. Schroen; Bret E. Field; Bozicevic, Field & Francis LLP

(57) ABSTRACT

Methods of evaluating homeostatic capacity of a subject are provided. Aspects of the methods include obtaining dynamic biometric data from the subject and evaluating the homoeostatic capacity of the subject from the obtained dynamic biometric data. Also provided are devices configured for use in practicing the methods. The methods and devices described herein find use in a variety of applications, e.g., health monitoring applications, treatment applications, dynamic diagnostic applications, etc.

16 Claims, 2 Drawing Sheets

Related U.S. Application Data

(60) Provisional application No. 62/254,583, filed on Nov. 12, 2015, provisional application No. 62/218,999, filed on Sep. 15, 2015, provisional application No. 62/128,816, filed on Mar. 5, 2015.

(51) Int. Cl.
| | |
|---|---|
| *A61B 5/0205* | (2006.01) |
| *A61B 5/021* | (2006.01) |
| *A61B 5/024* | (2006.01) |
| *A61B 5/01* | (2006.01) |
| *A61B 5/091* | (2006.01) |
| *A61B 5/08* | (2006.01) |
| *A61B 5/0533* | (2021.01) |
| *A61B 5/1455* | (2006.01) |
| *A61B 5/24* | (2021.01) |

(52) U.S. Cl.
CPC .......... *A61B 5/01* (2013.01); *A61B 5/021* (2013.01); *A61B 5/02405* (2013.01); *A61B 5/0533* (2013.01); *A61B 5/0816* (2013.01); *A61B 5/091* (2013.01); *A61B 5/14551* (2013.01); *A61B 5/24* (2021.01); *A61B 5/42* (2013.01); *A61B 5/4509* (2013.01); *A61B 5/4812* (2013.01); *A61B 5/4869* (2013.01); *A61B 2503/40* (2013.01)

(58) Field of Classification Search
CPC ..... A61B 5/4884; A61B 5/0205; A61B 5/021; A61B 2503/40
See application file for complete search history.

(56) References Cited

U.S. PATENT DOCUMENTS

| | | | |
|---|---|---|---|
| 7,363,076 B2 | 4/2008 | Yun et al. | |
| 7,676,269 B2 | 3/2010 | Yun et al. | |
| 7,738,952 B2 | 6/2010 | Yun et al. | |
| 7,767,713 B2 | 8/2010 | Yun et al. | |
| 7,899,527 B2 | 3/2011 | Yun et al. | |
| 7,966,072 B2 | 6/2011 | Yun et al. | |
| 8,121,690 B2 | 2/2012 | Yun et al. | |
| 8,160,696 B2 | 4/2012 | Bendett et al. | |
| 8,247,450 B2 | 8/2012 | Yun et al. | |
| 8,457,745 B1 | 6/2013 | Garcia et al. | |
| 8,491,459 B2 | 7/2013 | Yun | |
| 8,569,277 B2 | 10/2013 | Yun et al. | |
| 8,571,650 B2 | 10/2013 | Yun | |
| 8,691,877 B2 | 4/2014 | Yun et al. | |
| 8,722,016 B2 | 5/2014 | Yun | |
| 8,788,041 B2 | 7/2014 | Yun et al. | |
| 8,909,340 B2 | 12/2014 | Yun | |
| 2003/0097151 A1 | 5/2003 | Smedley et al. | |
| 2003/0195427 A1 | 10/2003 | Masakov et al. | |
| 2004/0086576 A1* | 5/2004 | Cianfarani | A23L 33/125 |
| | | | 424/655 |
| 2004/0230252 A1* | 11/2004 | Kullok | A61M 21/00 |
| | | | 607/48 |
| 2004/0249416 A1 | 12/2004 | Yun et al. | |
| 2005/0015122 A1 | 1/2005 | Mott et al. | |
| 2005/0021092 A1 | 1/2005 | Yun et al. | |
| 2005/0143788 A1 | 6/2005 | Yun et al. | |
| 2005/0153885 A1 | 7/2005 | Yun et al. | |
| 2005/0192637 A1 | 9/2005 | Girouard et al. | |
| 2005/0240241 A1 | 10/2005 | Yun et al. | |
| 2005/0256028 A1 | 11/2005 | Yun et al. | |
| 2005/0288721 A1 | 12/2005 | Girouard et al. | |
| 2006/0034847 A1 | 2/2006 | Yun et al. | |
| 2006/0035974 A1 | 2/2006 | Yun et al. | |
| 2006/0069012 A1 | 3/2006 | Yun et al. | |
| 2006/0116721 A1 | 6/2006 | Yun et al. | |
| 2006/0190052 A1 | 8/2006 | Yun et al. | |
| 2006/0206149 A1 | 9/2006 | Yun | |
| 2006/0216251 A1 | 9/2006 | Morariu | |
| 2007/0054871 A1* | 3/2007 | Pastore | A61K 48/0083 |
| | | | 514/44 R |
| 2007/0112327 A1 | 5/2007 | Yun et al. | |
| 2007/0208382 A1 | 9/2007 | Yun | |
| 2008/0075665 A1 | 3/2008 | Yun | |
| 2010/0119482 A1 | 5/2010 | Yun et al. | |
| 2010/0144691 A1 | 6/2010 | Yun et al. | |
| 2010/0260669 A1 | 10/2010 | Yun et al. | |
| 2010/0262220 A1 | 10/2010 | Yun | |
| 2010/0280116 A1 | 11/2010 | Yun et al. | |
| 2010/0286734 A1 | 11/2010 | Yun et al. | |
| 2010/0332443 A1 | 12/2010 | Gartenberg | |
| 2011/0015188 A1 | 1/2011 | Yun et al. | |
| 2011/0029030 A1 | 2/2011 | Yun et al. | |
| 2011/0152967 A1 | 6/2011 | Simon et al. | |
| 2011/0256097 A1 | 10/2011 | Yun et al. | |
| 2012/0270876 A1 | 10/2012 | Yun et al. | |
| 2013/0053817 A1 | 2/2013 | Yun | |
| 2013/0158423 A1 | 6/2013 | Kapoor | |
| 2014/0024079 A1 | 1/2014 | Yun | |
| 2014/0052211 A1 | 2/2014 | Yun | |
| 2014/0065129 A1 | 3/2014 | Yun et al. | |
| 2014/0086872 A1 | 3/2014 | Yun et al. | |
| 2014/0248217 A1 | 9/2014 | Yun | |
| 2014/0303236 A1 | 10/2014 | van Rooij et al. | |
| 2014/0350041 A1 | 11/2014 | Yun et al. | |
| 2014/0369969 A1 | 12/2014 | Yun | |
| 2015/0015122 A1 | 1/2015 | Koizumi et al. | |
| 2015/0025924 A1 | 1/2015 | Yun et al. | |
| 2015/0087608 A1 | 3/2015 | Yun | |
| 2015/0283265 A1 | 10/2015 | Peyman | |
| 2015/0359888 A1 | 12/2015 | Yun | |
| 2016/0213296 A1 | 7/2016 | Kikuchi et al. | |
| 2016/0375240 A1 | 12/2016 | Yanaki et al. | |
| 2018/0362623 A1 | 12/2018 | Tseng et al. | |

OTHER PUBLICATIONS

McCarty, et al. "Heart Rate Variability: New Perspectives on Physiological Mechanisms, Assessment of Self-regulatory Capacity, and Health Risk," Global Advances in Health and Medicine, vol. 4, No. 1, pp. 46-61, Jan. 2015. (Year: 2015).*

Russoniello et al., Heart rate variability and biological age: implications for health and gaming, Cyberpsychol Behav Soc Netw. Apr. 2013;16(4):302-8.

* cited by examiner

HOMEOSTATIC CAPACITY EVALUATION

CROSS-REFERENCE TO RELATED APPLICATIONS

This application is a continuation-in-part application of U.S. application Ser. No. 15/061,645 filed on Mar. 4, 2016, which application, pursuant to 35 U.S.C. § 119 (e), claims priority to U.S. Patent Provisional Patent Application Ser. No. 62/254,583 filed Nov. 12, 2015; U.S. Provisional Patent Application No. 62/218,999 filed Sep. 15, 2015; and U.S. Provisional Patent Application Ser. No. 62/128,816 filed Mar. 5, 2015; the disclosures of which applications are herein incorporated by reference.

INTRODUCTION

Homeostasis is a relatively stable state of equilibrium. Homeostatic capacity (or allostatic capacity, buffering capacity, compensatory capacity, or autoregulatory capacity) is the efficiency of an autoregulatory system to maintain functional homeostasis. The interaction of homeostatic capacity and stressors determines health.

Homeostatic capacity is so pervasively effective when we are young that we become more aware of it by its decline, especially after midlife, when recoveries from stressors—a late night, hangover, jet lag, cough, or injury—are readily noticeable. Our tolerance of contextual variation, such as changes in temperature and altitude, declines. Pupillary light reflex response diminishes, and menus are harder to read in low light. Roller coasters and somersaults leave us more discombobulated as our biologic Weeble™ loses its self-centering efficiency.

While these are just a few of the subjective losses of homeostatic capacity that we can feel, consider objective changes that we can't feel. The erosion of autoregulatory capacity of blood glucose, blood pressure, tumor surveillance, and inflammation could partially explain diabetes, hypertension, cancer, and various inflammatory diseases, respectively, independently of more widely accepted factors. Overall, as homeostatic tolerance for internal derangements declines with age, the same functions that promoted homeostasis during youth can behave dysfunctionally and promote secondary derangements in late adulthood (so-called antagonistic pleiotropy).

SUMMARY

Aspects of the present disclosure include a model for healthy, functional longevity based on evaluating and improving homeostatic capacity. The inventors of the present application have realized that various features of aging are epiphenomena of eroding homeostatic capacity that reduce our ability to contend with ubiquitous stressors and entropy. The inventors of the present application have realized that eroding homeostatic capacity is an Occam's razor that parsimoniously explains the arborized taxonomy and diverse features of aging, and that enhancing homeostatic capacity reverses the aging process and enables sustainable health.

Methods of evaluating homeostatic capacity of a subject are provided. Aspects of the methods include obtaining dynamic biometric data from the subject and evaluating the homeostatic capacity of the subject from the obtained dynamic biometric data. Also provided are devices configured for use in practicing the methods. The methods and devices described herein find use in a variety of applications, e.g., health monitoring applications, treatment applications, dynamic diagnostic applications, etc.

Aspects of the invention are based on the inventors' realization that for acute ailments, the proximate and ultimate goals of intervention are symmetric—restoring homeostasis. During the pre-modern era, when humans typically succumbed before senescence to acute insults such as trauma and infection, proximate interventions that acutely restored homeostasis (antibiotics, aseptic surgery) served patients well. Along with public health measures and vaccines, these treatments helped push median survivorship past the age of female reproductive senescence. However, for chronic conditions that predominate today, including senescence, Whack-a-Mole™ acute remediations for chronic dysfunctions can induce atrophy of homeostatic capacity, leading to tachyphylaxis, nefarious feed-forward decompensation, and progressive addiction to therapy. Many economic stakeholders benefit from the current approach, but the long-term benefit for patients is less clear. Extending lifespan without addressing senescence creates an older population that consumes more health care, creating an unsustainable, feed-forward cycle of cost escalation. A different framework is needed.

Aspects of the invention are based on the inventors' realization that for chronic conditions such as senescence (and others that occur at earlier ages), shifting the proximate goal to increasing homeostatic capacity is a path to the ultimate restoration of functional homeostasis. This small conceptual change portends a radical transformation in the way we currently treat many chronic conditions.

For instance, hypertension today is typically medicated with antihypertensives, a method that seemingly resolves the problem proximately but is prone to induce tachyphylaxis ultimately. Embodiments of the invention provide for administration of hormetic doses of prohypertensive interventions that are pulsed to promote allostatic response—the way exercise does—to lower baseline blood pressure.

Embodiments of the invention include employing eustress (or capacity building stress) to paradoxically promote homeostatic capacity as a way to ultimately ameliorate various chronic diseases.

Aspects of the invention include the use of transformed lifestyle interventions. Current static recommendations related to certain diets, exercise, stress reduction, and medi tation are, in some instances, shifted to dynamic recommendations that increase the body's tolerance and dynamic range. With homeostatic capacity building as the new goal of aspects of the present invention, lifestyle health emphasizes variance over fixed habits. Meditation is oscillated with exhilaration. Exercises vary in every dimension. Instead of eating a fixed diet such as vegan, some degree of variance that provides eustress is employed. Exposure to oscillations and variance in light and temperature, and other forms of eustress, are encouraged.

Aspects of the invention further include fundamental resolutions—cures or near-cures where the benefits are sustained with reduced dependence on repeat or ongoing intervention—for chronic conditions, including senescence. In that regard, embodiments of the invention employ editing genes and pathways—e.g., as involved in biologic clocks, repair mechanisms, control systems, or energetics—that affect homeostatic capacity. System dyssynchrony, loss of power, and desensitization to stimuli, which impair autoregulatory feedback loops and homeostatic capacity, are among underlying common factors in cell aging that could fractally connect cell senescence regulation to organismal senescence.

The present inventors have realized that dynamic systems such as biology are better evaluated with dynamic models than static ones. Yet we have heretofore been largely reliant on state variables as biomarkers. Annual checks of heart rate, blood pressure, glucose, and cholesterol levels to assess health risks are tantamount to a seismic engineer relying on the degree of angular declination, instead of resilience, to predict collapse risk. Biologists, too, can add dynamic measures to current state variables to evaluate systems and homeostatic capacity—a concept analogous to resilience, strength, robustness, antifragility, and antifrailty. The present inventors have realized that biology is better explored four dimensionally, with more time series data and better temporal resolution. Aspects of the invention include a broad array of diagnostic tests with capabilities for continuous or high-frequency sampling.

In some instances, a system's potential homeostatic performance under all possible conditions, including every magnitude, type, pattern, and duration of stress, cannot be reduced into a single measure. However, approximations of homeostatic capacity are possible through a composite of state variables, dynamic diagnostics, response diagnostics, and stress testing—assessment after contextual changes or allostatic loads. Examples of dynamic response tests include baroreceptor sensitivity, heart rate variability, flow-mediated vasodilation, postprandial glucose and triglyceride tolerance tests, gait balance, pupillary light reflex, and recovery time after cardiac stress. In some embodiments, measures of resilience correlate with chronologic age more than the underlying state variables (example: heart rate recovery after cardiac stress versus resting heart rate).

Aspects of the invention include standards that allow approximations of an individual's homeostatic capacity. Population-wide, age-based normative values for a large panel of relatively uncorrelated measures of homeostatic capacity may be employed. The normative values at peak levels during youth can be used as benchmarks for understanding where an individual's measures of homeostatic capacity stand as they advance in chronologic age. Alternatively, the measure of homeostatic capacity can be personalized such that each individual's peak values can be used as self-referential benchmarks over time.

In some instances, homeostatic capacity levels beyond normative peak levels are pursued not only by elite athletes and military personnel for the purposes of human performance, but also by the broader population for the purposes of health, e.g., through training, capacity building, and intervention. Interventions that improve a large composite panel of relatively uncorrelated measures of homeostatic capacity—functional outcomes—are employed in some instances to obtain a systemic benefit. This category of interventions will fundamentally transform the future of human health.

Homeostatic capacity is a fundamental trait of living systems, filtered by evolution at all scales of biology and all temporal epochs. Aspects of the present disclosure include innovations that fundamentally increase homeostatic capacity which are a foundation to developing strategies that will help avert the natural aging process and promote functional longevity. The end of aging would be the end of healthcare as we know it. The feed-forward relationship between healthcare innovation and increasing future consumption would finally be decoupled. Restoration, augmentation and indefinite sustainment of homeostatic capacity, e.g., as described herein, allows humans to persist at low annual mortality rates currently enjoyed by young adults. Healthy lifespan telescopes to a number of years that might have once seemed unimaginable. Human capacity is thus unleashed.

Aspects of the invention include employing a single intervention to modulate, e.g., enhance, homeostatic capacity of two or more, such as three or more, different, and in some instances seemingly unrelated, systems, e.g., as described above. For example, aspects of the invention include employing a single intervention to improve the homeostatic capacity of a composite of seemingly unrelated systems.

In some instances, homeostatic capacity is enhanced according to the methods described in U.S. application Ser. No. 15/363,980 entitled "Methods of Enhancing Homeostatic Capacity in a Subject by Modulating Homeostatic System Synchrony, and Devices for Use in Practicing the Same," the disclosure of which is herein incorporated by reference.

In some instances, homeostatic capacity is enhanced according to the methods described in U.S. application Ser. No. 15/363,988 entitled "Methods of Enhancing Homeostatic Capacity in a Subject by Increasing Homeostatic System Component Responsiveness, and Devices for Use in Practicing the Same," the disclosure of which is herein incorporated by reference.

DETAILED DESCRIPTION

Figure 1:
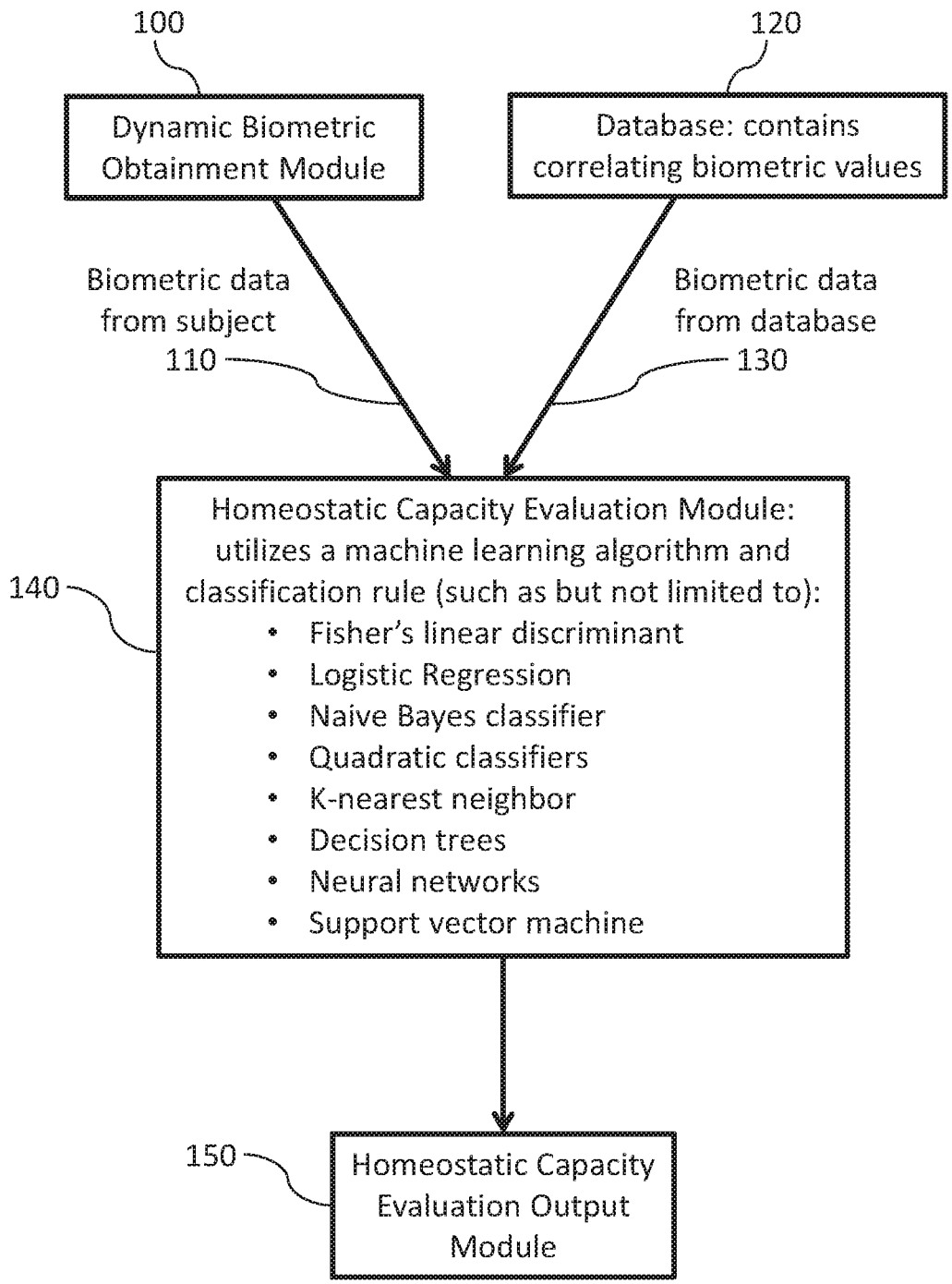
FIG. 1 is a flow chart illustrating one embodiment of a method for evaluating homeostatic capacity of a subject.

Methods of evaluating homeostatic capacity of a subject are provided. Aspects of the methods include obtaining dynamic biometric data from the subject and evaluating the homoeostatic capacity of the subject from the obtained dynamic biometric data. Also provided are devices configured for use in practicing the methods. The methods and devices described herein find use in a variety of applications, e.g., health monitoring applications, treatment applications, dynamic diagnostic applications, etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the invention, aspects of embodiments of methods of evaluating homeostatic capacity are described first in greater detail, followed by a description of representative devices that find use in practicing such methods. Next, a review of various applications in which the methods and devices find use, is provided.

Methods of Homeostatic Capacity Evaluation

As summarized above, methods for evaluating homeostatic capacity of a subject are provided. Homeostatic capacity refers to the ability of a subject to maintain relatively constant conditions in the internal environment while continuously interacting with and adjusting to changes originating within or outside the system. By "evaluating" is meant assessing, analyzing or assaying to provide a form of measurement, e.g., in the form of a determination or proxy thereof, of the homeostatic capacity of the subject. The evaluations that may be made may be quantitative and/or qualitative determinations, and be represented as a value or set of values, as desired.

Aspects of the methods include obtaining dynamic biometric data from a subject. The phrase "biometric data" is employed to refer to a measure of a biometric parameter that relates to the physiology of a living organism, e.g., as described below. As such, the biometric parameter which is employed in methods of the invention to obtain the biometric data may be a parameter that provides information about an organism's vital functions, including growth and development, the absorption and processing of nutrients, the synthesis and distribution of proteins and other organic molecules, the functioning of different tissues, organs, and other anatomic structures; the psychological and/or behavioral state of the subject, e.g., mental and/or cognitive state of the subject, which may be subjective or objective, self-reported or third party observed, as desired; etc.

Biometric parameters that are measured may vary widely, where examples of such parameters include physiological, chemical, electrical, behavioral, psychological, etc., based parameters, as well as variations and derivatives thereof. Biometric parameters of interest include, but are not limited to: physical parameters, e.g., blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; nerve conduction measures, e.g., motor NCS, sensory NCS, F-wave study, H-reflex study, spf-NCS, etc.; and the like, and combinations thereof; sample analysis obtainable parameters, e.g., pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apolipoprotein B100/A1 ratio, white blood cell count, cholesterol, oxygen saturation, and the like, and combinations thereof. Dynamic biometric data may be made up of information about a single type of biometric parameter, or two or more different types of biometric parameters. The biometric data employed in methods of the invention may thus be made up of information obtained by measuring or assessing one or more biometric parameters, such as the ones listed above.

As summarized above, the biometric data that is obtained and employed in methods of the invention is dynamic biometric data. By "dynamic biometric data" is meant biometric data that incorporates some type of change component, as opposed to static biometric data. The change component may vary widely, where examples of change components include, but are not limited to components that are: temporal and/or in response to an applied stimulus and/or in response to withdrawal of stimulus and/or in response to a change in the contextual environment of the subject. For example, the dynamic biometric data that is obtained may be biometric data obtained over a given period of time. The given period of time may vary, ranging in some instances from 0.1 seconds to 24 hours, such as 1 second to 12 hours, e.g., 1 second to 1 hour, including 1 second to 1 minute. Where the dynamic biometric data is data obtained over a given period of time, the data may be obtained continuously over that period of time or at one or more distinct points during that period of time. For example, the biometric parameter(s) that is monitored in order to obtain biometric data may be monitored continuously during the given period of time, i.e., it may be obtained in an uninterrupted manner, i.e., without cessation, during the given period of time. Alternatively, the biometric parameter(s) that is monitored in order to obtain biometric data may be monitored intermittently during the given period of time, i.e., it may be obtained at one or more points over the given period of time, with an interval between points at which it is not obtained. In some embodiments, the interval may vary, ranging, for example, from 0.01 sec to 60 minutes or longer, such as 0.1 to 60 s. In some instances, the dynamic biometric data is obtained by evaluating a biometric parameter for a rate of change over a period of time. As such, methods may include obtaining information about the speed at which a biometric parameter of interest changes over a given period of period of time. Obtaining dynamic biometric data as described above provides for numerous benefits, including increases in temporal resolution, as compared to single point in time data. Dynamic biometric data as obtained herein provides a truer and more meaningful measure of the biometric value(s) of interest, as compared to single point in time measurements.

Dynamic biometric data of interest also includes biometric data that is obtained by evaluating a biometric parameter for a change in response to an applied stimulus. Such biometric data may include data that is obtained before and/or after application of the stimulus to the subject. In some instances, the biometric data may be obtained over a given period of time that spans or follows the application of the stimulus to the subject. This type of biometric data may be viewed as biometric data that is obtained over a given period of time in conjunction with application of a stimulus to the subject being evaluated. The applied stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also includes biometric data that is obtained by evaluating a biometric parameter for a change in response to withdrawal of a stimulus. Such biometric data may include data that is obtained before and/or after withdrawal (e.g., blockage) of the stimulus to the subject. In some instances, the biometric data may be obtained over a given period of time that spans or follows the withdrawal of the stimulus to the subject. This type of biometric data may be viewed as biometric data that is obtained over a given period of time in conjunction with withdrawal of a stimulus to the subject being evaluated. The withdrawn stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

Dynamic biometric data of interest also includes biometric data that is obtained by evaluating a biometric parameter for a change in response to modulation of the contextual environment of the subject. By contextual environment of the subject is meant the perceived environment of the subject. Such biometric data may include data that is obtained before and/or after the modulation in the contextual environment of the subject. In some instances, the biometric data may be obtained over a given period of time that spans or follows the modulation of the contextual environment of the subject. This type of biometric data may be viewed as biometric data that is obtained over a given period of time in conjunction with modulation of the contextual environment of the subject. The modulation of the contextual environment of the subject may vary, where contextual modulations of interest include, but are not limited to, change in day and night duration, change in temperature, change in humidity, change in elevation, change in atmosphere, and the like.

Dynamic biometric data of interest also includes biometric data that is obtained by evaluating a biometric parameter for a change in response to modulation of the behavioral aspect of the subject. By behavioral aspect of the subject is meant an observable activity of the subject. Such biometric data may include data that is obtained before and/or after the modulation of the behavioral aspect of the subject. In some instances, the biometric data may be obtained over a given period of time that spans or follows the modulation of the behavioral aspect of the subject. This type of biometric data may be viewed as biometric data that is obtained over a given period of time in conjunction with modulation of the behavioral aspect of the subject. The modulation of the behavioral aspect of the subject may vary, where behavioral modulations of interest include, but are not limited to, dietary changes, sleep pattern changes, activity level changes, and the like. It is noted that the dynamic biometric data that is employed in methods of the invention may be the data that is directly obtained from a suitable sensor, or a derivative thereof. As such, derivative measurements of dynamic biometric data may be obtained in methods of the invention, include second, third, etc. order derivative data. For example, instead of or in addition to employing a measured change in a parameter, such as acceleration or deceleration, one may employ the speed of the measured change in the parameter, i.e. first derivative.

As reviewed above, a variety of different biometric parameters may be measured to obtain the dynamic biometric data. The method by which the biometric data is obtained may vary depending on the nature of the biometric parameter that is monitored. In some instances, the method employed to obtain the biometric data includes physically monitoring the subject to obtain the dynamic biometric data. For example, physical monitoring of the subject may be employed where the biometric parameter is one or more of blood pressure, orthostatic hypotension, pulse pressure, heart rate, heart rate variability (HRV), heart rate recovery, resting heart rate, respiration rate, forced expiratory volume, forced vital capacity, temperature, core temperature, galvanic skin response, gastrointestinal motility, sleep cycle, VO2 max, bone density, weight, body mass index (BMI), bone density, waist to hip ratio, waist circumference, other obesity measures (e.g., volume displacement, Dual Energy X-ray Absorptiometry (i.e., DEXA), etc.), baroreceptor sensitivity, oxygen saturation, nervous system activity measurements, including electrical potential measurements, such as spontaneous electrical potential measurements, e.g., EEG, EMG EKG, evoked electrical potential measurements, e.g., sensory evoked potentials (such as auditory invoked potentials (e.g., brain stem evoked response or potential (ABER or ABEP), visual evoked potentials, tactile or somatosensory evoked potentials, laser evoked potentials), motor evoked potentials, etc.; nerve conduction measures, e.g., motor NCS, sensory NCS, F-wave study, H-reflex study, spf-NCS, etc.; and combinations thereof. Any convenient protocol for physically monitoring a subject for one or more of the above biometric parameters may be employed, and methods for physically monitoring each are known in the art. For example, where the biometric parameter of interest is HRV, the physical monitoring may include measures such as low frequency peak ("LF"), high frequency peak ("HF"), and the LF/HF ratio to determine HRV and obtain the HRV derived biometric data.

In some embodiments, the dynamic biometric data is obtained by a method that includes analyzing a sample from the subject to obtain the dynamic biometric data. The sample that is analyzed may vary, where samples of interest include, but are not limited to: urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, and the like, and may employ conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like. Biometric parameters that may be monitored by evaluating a sample from the subject include, but are not limited to: pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, creatinine, urea nitrogen, c-reactive protein, hemoglobin, triglycerides, lipoproteins, apolipoprotein B100/A1 ratio, white blood cell count, cholesterol, oxygen saturation, and combinations thereof.

Any convenient protocol for physically monitoring a subject for one or more of the above biometric parameters may be employed, and methods for testing a sample for monitoring each are known in the art. In some instances, the dynamic biometric data is obtained by both physically monitoring the subject and by assaying a sample from the subject, e.g., as described above. Of interest in certain embodiments are virtual reality (VR) mediated protocols.

Aspects of the methods further include evaluating the homoeostatic capacity of the subject from the dynamic biometric data. As such, following obtainment of the dynamic biometric data, the homeostatic capacity of the subject is evaluated based on the obtained dynamic biometric data. Any convenient protocol may be employed to evaluate the homeostatic capacity of the subject based on the obtained dynamic biometric data. For example, the obtained dynamic biometric data may be compared to control or reference sets of dynamic biometric data to obtain the homeostatic capacity evaluation. In some instances, the obtained dynamic biometric data may be compared to a suitable database of control or reference sets to obtain the homeostatic capacity evaluation. The control or references sets of data may be made up of data obtained from multiple different individuals of known homeostatic capacity. The data may be made up from individuals of a variety of different ages and health, including from young and old individuals, as well as healthy and diseased individuals, as desired. Any suitable comparison algorithm may be employed, and the output homeostatic capacity evaluation may be produced in a variety of different formats or configurations. This homeostatic capacity evaluation step may be performed using a suitable functional module of a computing device/system, e.g., as described in greater detail below.

The homeostatic capacity evaluation that is provided by methods of the invention may vary, as desired. For example, the evaluation may be an output in the form of a qualitative assessment, e.g., bad, poor, average, good and exceptional, etc. The output may be in the form of a quantitative assessment, e.g., where the homeostatic capacity evaluation output a number selected from a numerical scale. The homeostatic capacity evaluation output may provide assessment with respect to a number of different homeostatic capacity parameters, such as but not limited to: the robustness, dynamic range, resilience, coping mechanism, antifragility, etc., of the homeostatic capacity of the individual. The output showing the homeostatic capacity of the animal/person may be provided as a proxy for the biological age (as opposed to the chronological age) of the subject, e.g., by using statistical correlations relative to the general population. For example, the homeostatic capacity evaluation produced from dynamic biometric data from a 50 year old professional cyclist in great condition could suggest that the "biological age" of that person based on homeostatic capacity measures is actually much younger, e.g., that of a 35 years old from the general population. In some instances, the homeostatic capacity evaluation is one that is prepared by comparing the obtained dynamic biometric data to a database that includes data comprising statistically meaningful values that correlate each biometric value and/or a combination of the biometric values of interest to the values of different ages or age ranges of cohorts for the same biometric value(s). For example, in instances where the obtained biometric data may be from an individual or animal that is 30 years of age, the homeostatic capacity evaluation may be performed by comparing the obtained biometric data to data obtained from healthy individuals from a variety of ages ranging from 20 to 80 years, and show a correlation to a certain age of the individual as a whole or certain systems thereof, e.g., cardiovascular system, neurological system, reproductive system, etc. For example, the output homeostatic capacity evaluating may be an overall composite number, e.g., that the individual has the homeostatic capacity of a 32 year old, or be more granular with respect to particular biological systems of the individual, e.g., where the output is that the system provides a homeostatic capacity evaluation in which the subject has a cardiovascular system of a 25 year old but the nervous system of a 35 year old. In such instances, these sub-categories could be at systems levels of the body and could be more granular, e.g., portions of systems.

The methods described herein may be employed with a variety of different types of subjects, i.e., animals, where the animals may be "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In some instances, the subjects or patients are humans or laboratory research animals.

In some embodiments, the methods may further include modulating the homoeostatic capacity of the subject following obtainment of the homeostatic capacity evaluation of the subject. For example, the methods may include at least partially restoring the homeostatic capacity following evaluation of such. By "at least partially restoring the homeostatic capacity of the subject" is meant that the homeostatic capacity of the subject is enhanced or improved, e.g., to that of a target value, which target value may be a "normal" value or greater than a normal value, e.g., a super-normal value. By "normal" is meant the homeostatic capacity of a healthy subject of a particular age. In certain embodiments, the healthy subject is a healthy human at an age after puberty, e.g., 18 year old, 19 year old, 20 year old, 21 year old, 22 year old, 23 year old, 24 year old, 25 year old, 26 year old, 27 year old, 28 year old, 29 year old, 30 year old, 31 year old, 32 year old, 33 year old 34 year old, 35 year old, 36 year old, 37 year old, 38 year old, 39 year old, 40 year old, 41 year old, 42 year old, 43 year old, 44 year old, 45 year old, 46 year old, 47 year old, 48 year old, 49 year old or 50 year old. In some instances, the normal function with respect to homeostatic capacity is that of a healthy human 25 year old. By super normal value is meant the homeostatic capacity of a subject of have greater than normal homeostatic capacity, e.g., that of an athlete, etc. The magnitude of difference between normal and super normal may vary, and in some instances may be 5% or greater, such as 10% or greater, including 15%, 20% or 25% or greater, where in some instances the target super normal homeostatic capacity is 5% to 75% greater than of a normal homeostatic capacity. In some instances, the methods include modulating the homeostatic capacity of the subject to that it is at least closer to a target homeostatic capacity. By "at least closer" is meant, in some instances, that the target homeostatic capacity is restored to be 50% or more, e.g., 75% or more of the target function, such as 80% or more of the target function, including 90% or more of the target function, e.g., 95% or more of the target function, including 99% or more of the target function.

Modulation of the homeostatic capacity of a subject as described above can be achieved using any suitable protocol, including, but not limited to electrical and/or pharmacologic and/or physical and/or chemical and/or psychological and/or environmental and/or behavioral protocols, e.g., as described in greater detail below.

In some instances, the methods may include use of one or more static measures of homeostatic capacity. Such measures may be used as separate measures, or composites of dynamic and static measurements may be employed.

Embodiments of the methods result in rapid restoration of homeostatic capacity of the subject. For example, in some instances homeostatic capacity may be restored in 72 hours or less relative to the onset of autonomic modulation, such as in 48 hours or less, 24 hours or less, or 12 hours or less relative to the onset of autonomic modulation. In other embodiments of the methods, the restoration of homeostatic capacity may take a longer period of time, e.g., 1 or more days or longer, 1 or more months or longer, including 1 or more years or longer. The therapeutic protocol employed may be continuously or periodically applied, e.g., where the protocol is mediated by an implanted device that provides for continuous, intermittent or period administration of electrical and/or pharmacological treatment, e.g., as described in greater detail below.

Utility

The subject methods find use in a variety of different applications.

Applications of interest include, but are not limited to: health and wellness monitoring applications; diagnostic applications; preventative applications; treatment applications; etc.

Health/Wellness Applications

For example, the methods described herein may be employed in various health and wellness monitoring applications, e.g., by individuals monitoring themselves or interested stakeholders, e.g., health care professionals, physical trainers, family or friends, etc., monitoring the individuals. For example, the methods may be employed by individuals to monitor their homeostatic capacity on an ongoing basis, e.g., so that they can monitor their health and well-being over time. The individuals may use the homeostatic capacity evaluation to make lifestyle changes, e.g., changes in diet and/or exercise. Alternatively or in addition, the methods may be employed by a stakeholder having an interest in the health of an individual, such as the stakeholders listed above.

Diagnostic Applications

In yet other instances, the methods may be employed in at least the prediction of the presence of, if not diagnosis of, a condition that is present or may occur in a subject, which may be a disease or other condition, such as the conditions described below. For example, in some embodiments the homeostatic capacity evaluation or underlying data thereof, e.g., dynamic measurement data, may be employed to predict, if not diagnose, the presence of a disease condition in the subject. In some instances, the methods may be employed to predict the predisposition of a subject for developing a disease condition in the future, and may further include developing a regimen configured to delay or prevent occurrence of the predicted condition. In some instances, the methods may be employed to predict the impending occurrence in a subject a disease condition or symptom, e.g., episode or acute condition, thereof, e.g., of an allergic, e.g., anaphylaxis, episode; an autistic episode; etc. In such dynamic diagnostic applications, any convenient dynamic measure may be employed, such as those described above, e.g., heart rate variability readings, EEG readings, EKG readings, etc. The dynamic measure data may be employed raw in an algorithm used to predict the impending occurrence, or may be processed and then used to predict the impending occurrence, e.g., an HC evaluation obtained from the raw data may be employed to predict the impending occurrence, as desired. For example, dynamic diagnostic applications of the invention include obtaining dynamic measures of one or more of HRV, EEG and EKG, e.g., as described above, and using the resultant data to predict the impending occurrence of a condition symptom or episode, e.g., an allergic response, e.g., an anaphylactic response, where the prediction may be made some time prior to the occurrence, e.g., 5 seconds or more, 10 seconds or more, 30 seconds or more, 60 seconds or more, 5 minutes or more, 10 minutes or more, 15 minutes or more, 30 minutes or more, 60 minutes or more, 2 hours or more, 6 hours or more, 12 hours or more, 24 hours or more, before the occurrence of the condition symptom or episode. In such instances, the prediction of the future occurrence may be coupled with appropriate therapeutic intervention, e.g., to prevent the occurrence, ameliorate the magnitude of the occurrence, reduce the impact on others of the occurrence, etc.

Treatment Applications

In some instances, the methods find use as a component of the treatment of a variety of different conditions. By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

Non-limiting examples of disease conditions that may be treated by practice of the methods include, but are not limited to: Examples of conditions that may be treated with the methods of the subject invention include, but are not limited to, cardiovascular diseases, e.g., atherosclerosis, coronary artery disease, hypertension, hyperlipidemia, cardiomyopathy, volume retention; neurodegenerative diseases, e.g., Alzheimer's disease, Pick's disease, dementia, delirium, Parkinson's disease, amyotrophic lateral sclerosis; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma, CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant-related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyperreninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shy dragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effusion, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

In some instances, at least partial restoration of the homoeostatic capacity of a subject results in treatment of a condition caused by sympathetic bias. Conditions that are caused by a sympathetic bias include, but are not limited to aging related diseases, such as but not limited to: cardiovascular disease, cancer, arthritis, cataracts, osteoporosis, type 2 diabetes, hypertension; shy dragers, multi-system atrophy, age related inflammation conditions and diabetes.

In some instances, at least partial restoration of the homoeostatic capacity of a subject results in treatment of a condition caused by parasympathetic bias. Conditions that are caused by a parasympathetic bias include, but are not limited to an allergy, common cold, eczema, asthma, anaphylaxis, attention deficit hyperactive disorder (ADHD), autism, obesity, depression, Tourette's syndrome, hay fever, cough, fatigue, hypothyroidism, chronic fatigue syndrome, environmental sensitivity syndrome, shock, sepsis, food allergy and food allergy syndrome.

Also of interest are non-disease conditions, where such non-disease conditions include, but are not limited to: aging, sleep deprivation, veisalgia, and the like.

As such, aspects of the invention include methods that further include treating a subject for a condition. Embodiments of such methods include: obtaining a dynamic measure of homeostatic capacity for the subject, e.g., as described above, and administering a therapy to the subject in a manner sufficient to modulate the subject's dynamic measure of homeostatic capacity to more closely approximate a target dynamic measure of homeostatic capacity and treat the subject for the condition. In some instances, the methods may include a homeostatic capacity measurement that is based on one or more static measures of homeostatic capacity. Such measures may be used as separate measures, or composites of dynamic and static measurements may be employed.

In these embodiments of the invention, any convenient therapy may be administered to a subject. Therapies that may be employed include, but are not limited to: traditional medical therapies, e.g., electrical therapies, pharmacological therapies, electropharmaceuticals, etc.; and non-traditional medical therapies, e.g., homeopathic therapies, acupuncture, acupressure, mechanical manipulation, e.g., chiropractic therapies, laser therapy, e.g., to the vertex or other physiological locations, etc. Therapies of interest may also be categorized as physical, chemical, psychological, environmental, electrical, behavioral, pharmacological, etc. Specific types of therapies of interest are now reviewed in greater detail.

ANS Modulation

In some instances, the administered therapy is one that modulates the autonomic nervous system of the subject. The autonomic nervous system ("ANS") is that portion of the nervous system that is not the somatic nervous system. The ANS controls individual organ function and homeostasis. For the most part, the ANS is not subject to voluntary control. The ANS is also commonly referred to as the visceral or automatic system. The ANS can be viewed as a "real-time" regulator of physiological functions that extracts features from the environment and, based on that information, allocates an organism's internal resources to perform physiological functions for the benefit of the organism, e.g., responds to environment conditions in a manner that is advantageous to the organism. The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs; lungs; stomach; colon; bladder; visual accommodation, secretions from exocrine and endocrine glands, etc. The ANS does this through a series of nerve fibers and more specifically through efferent and afferent nerves.

The ANS acts through a balance of its two components: the sympathetic nervous system and parasympathetic nervous system, which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands).

By "modulating" is meant altering or changing one or more aspects or components to provide a change, alteration or shift in another aspect or component. Modulating autonomic function is achieved by modulating at least one portion of the subject's autonomic nervous system. By "modulating at least one portion of the subject's autonomic nervous system" is meant altering or changing at least a portion of an autonomic nervous system by a means to provide a change, alteration or shift in at least one component or aspect of the autonomic nervous system.

In some instances of the subject methods, modulation of the autonomic nervous system includes modulating the parasympathetic and/or sympathetic activity in the subject. "Parasympathetic activity" refers to activity of the parasympathetic nervous system whereas "sympathetic activity" refers to activity of the sympathetic nervous system.

In some instances, modulation results in at least one of decreasing parasympathetic activity and/or increasing sympathetic activity in a subject to improve a condition caused by parasympathetic bias. In other embodiments, the modulation results in at least one of decreasing sympathetic activity and/or increasing parasympathetic activity in a subject to improve a condition caused by sympathetic bias.

Therapeutic modalities may employ modulation of activity in or more components of the nervous system. The nervous system includes the spinal cord and the pairs of nerves along the spinal cord which are known as spinal nerves. The spinal nerves include both dorsal and ventral branches which fuse in the intravertebral foramen to create a mixed nerve. Methods employed in the invention may modulate only one of the dorsal or ventral branches, or both of the dorsal and ventral branches, where when both of the dorsal and ventral branches are modulated, the modulation may be the same or different, e.g., where the two branches are differentially modulated.

Modulation of the autonomic nervous system may be carried out using any suitable protocol, including, but not limited to: electrical and/or pharmacologic and/or physical and/or chemical and/or psychological and/or environmental protocols, e.g., as described below. The modulation of the ANS provides, in some instances, an increase in function of at least a portion of the autonomic system, e.g., increase function in at least one sympathetic or parasympathetic nerve fiber, and/or provides, in some instances, a decrease in function or dampening of a portion of the autonomic system, e.g., may inhibit activity in at least one sympathetic or parasympathetic nerve fiber or inhibit nerve pulse transmission.

In some instances, the modulation that is achieved in practicing methods of the invention may be quantified. One way of quantifying modulation of at least one portion of the subject's autonomic nervous system is the parasympathetic/sympathetic activity ratio. By "parasympathetic/sympathetic activity ratio" is meant the ratio of activity of the sympathetic nervous system to the activity of the parasympathetic nervous system. As such, methods according to certain embodiments include modulating a sympathetic/parasympathetic activity ratio in the subject.

In some instances, the ANS is modulated in a manner sufficient to shift or change parasympathetic activity and/or sympathetic activity from a first state to a second state, where the second state is characterized by an increase or decrease in the sympathetic activity/parasympathetic activity ratio relative to the first state.

Accordingly, some embodiments of the subject invention include modulating at least a portion of a subject's autonomic nervous system to increase the sympathetic activity/parasympathetic activity ratio, i.e., to increase sympathetic activity relative to parasympathetic activity (in other words to decrease parasympathetic activity relative to sympathetic activity) so as to treat a subject for a condition that can be treated by such modulation (e.g., a condition caused by parasympathetic bias). Alternatively or in addition to stimulating at least one sympathetic nerve fiber to increase activity, increasing the sympathetic activity/parasympathetic activity ratio may be achieved by inhibiting activity in the parasympathetic system.

Other embodiments of the subject invention include modulating a subject's autonomic nervous system to decrease the sympathetic activity/parasympathetic activity ratio, i.e., to decrease sympathetic activity relative to parasympathetic activity (in other words, to increase parasympathetic activity relative to sympathetic activity) so as to treat a subject for a condition that can be treated by such modulation (e.g., a condition caused by sympathetic bias).

As will be described in greater detail below, while the ratio of sympathetic function/parasympathetic function may be modulated according to embodiments of the subject invention to treat or improve a subject for a condition (e.g., aging associated conditions) the net result may be a parasympathetic bias (i.e., a parasympathetic dominance), a sympathetic bias (i.e., sympathetic dominance), or the activities of the sympathetic system and parasympathetic system may be substantially equal (i.e., neither is dominant).

By "bias", is meant that the particular "biased" component of the autonomic nervous system has a higher activity level than the other component. For example, a parasympathetic bias refers to a higher level of parasympathetic activity than sympathetic activity, and vice versa, where such bias may be systemic or localized. As such, by "vagal bias", is meant that that the particular biased component of the autonomic nervous system that has a higher activity level than the other component is the vagus nerve or a portion of the autonomic nervous system associated with the vagus nerve. Vagal bias may be characterized by one or more of vagal dominance, vagal hypersensitivity and/or sympathetic insufficiency. The net result of the subject methods to treat a condition may be higher or greater sympathetic activity relative to parasympathetic activity in at least the area of the targeted autonomic system (i.e., that portion in need of modulation), or substantially equal activity levels of sympathetic activity and parasympathetic activity.

As noted above, in certain embodiments activity in at least a portion of the autonomic nervous system is increased. For example, activity in at least a portion of the ANS that is involved the sympathetic nervous system may be increased such that at least a portion of the sympathetic nervous system may be "up-regulated". In other instances, any portion of the ANS that is involved in the parasympathetic system, e.g., one or more nerve fibers, may be stimulated to increase parasympathetic activity to provide the desired ratio of parasympathetic/sympathetic activity. In other words, activity in at least a portion of the parasympathetic nervous system may be increased such that at least a portion of the parasympathetic nervous system may be "up-regulated".

In certain embodiments, increasing activity in, or up-regulating, at least a part of the sympathetic system may be desired in instances where, prior to the application of autonomic nervous system-modulating agent, parasympathetic activity is higher than desired, e.g., higher than sympathetic activity (e.g., there exists a relative parasympathetic bias) and as such the subject methods may be employed to increase sympathetic activity to a level above or rather to a level that is greater than parasympathetic activity or may be employed to modulate the differential between the parasympathetic-sympathetic systems such that the result of increasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase sympathetic activity above that of parasympathetic activity and/or may be employed to modulate (increase or decrease) the differential between the two systems, but in certain embodiments may be employed to decrease the parasympathetic activity/sympathetic activity ratio.

In other embodiments, increasing activity in, or up-regulating, at least a part of the parasympathetic system may be desired in instances where, prior to the application of autonomic nervous system-modulating agent, sympathetic activity is higher than desired, e.g., higher than parasympathetic activity (e.g., there exists a relative sympathetic bias) and as such the subject methods may be employed to increase parasympathetic activity to a level above or rather to a level that is greater than sympathetic activity or may be employed to modulate the differential between the parasympathetic-sympathetic systems such that the result of increasing parasympathetic activity may be a parasympathetic bias, sympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase parasympathetic activity above that of sympathetic activity and/or may be employed to modulate (increase or decrease) the differential between the two systems, but in certain embodiments may be employed to decrease the parasympathetic activity/sympathetic activity ratio.

In certain embodiments, a parasympathetic bias may be the normal state, but the ratio of the two systems may be abnormal or otherwise contributing to a condition. Increasing sympathetic bias may also be desired in instances where, prior to the restoration of the normal function of a central nervous system endocrine gland, sympathetic activity is higher than the parasympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low).

For example, such instances may occur where a subject has normal or above normal sympathetic function, but also has elevated parasympathetic function. Other instances may include below normal sympathetic function, but normal or elevated parasympathetic function, etc. It may also be desirable to increase sympathetic function in instances where the respective activities of the two system are analogous or approximately equal, including equal, prior to increasing activity in the sympathetic system, but the level of one or both is abnormally high or abnormally low. The above-described examples of instances where increasing sympathetic activity may be desired is exemplary only and is in no way intended to limit the scope of the invention and other instances where increasing sympathetic activity may be desired will be apparent to those of skill in the art.

In other embodiments, a sympathetic bias may be the normal state, but the ratio of the two systems may be abnormal or otherwise contributing to a condition. Increasing parasympathetic bias may also be desired in instances where, prior to the restoration of the normal function of a central nervous system endocrine gland, parasympathetic activity is higher than the sympathetic activity, but the differential between the two needs to be modulated such as increased further, e.g., the parasympathetic activity is normal or above normal (i.e., abnormally high) and/or the sympathetic activity is normal or below normal (i.e., abnormally low) or above normal (i.e., abnormally low).

For example, such instances may occur where a subject has normal or above normal parasympathetic function, but also has elevated sympathetic function. Other instances may include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low. The above-described examples of instances where increasing parasympathetic activity may be desired is exemplary only and is in no way intended to limit the scope of the invention and other instances where increasing sympathetic activity may be desired will be apparent to those of skill in the art.

As noted above, in certain embodiments, activity in at least a portion of the ANS may be inhibited to modulate at least a portion of the autonomic nervous system. Inhibiting or "down-regulating" activity in at least a part of the autonomic nervous system, may be desired in instances where, the sympathetic or parasympathetic activity is higher than desired. For example, parasympathetic activity may be higher than the sympathetic activity (i.e., there exists a parasympathetic bias) or parasympathetic activity may be less than or approximately equal to, including equal, to sympathetic activity, and the subject methods may be employed to modulate the differential between the parasympathetic-sympathetic systems such that the net result of decreasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., increased or reduced in certain embodiments. Accordingly, the subject methods may be employed to decrease parasympathetic activity below that of sympathetic activity and/or may be employed to modulate (decrease or increase) the differential between the two systems, where in certain embodiments may be employed to decrease the ratio of parasympathetic activity to sympathetic activity.

For example, decreasing activity in at least a portion of the parasympathetic system may be employed where there is a normal or an abnormally low sympathetic function and/or abnormally high parasympathetic function. Such may also be desired in instances where, prior to decreasing parasympathetic function in, e.g., at least one parasympathetic nerve fiber, sympathetic activity is higher than the parasympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing parasympathetic activity may be desired is exemplary only and is in no way intended to limit the scope of the invention and other instances where decreasing parasympathetic activity to provide an increase in the parasympathetic activity/sympathetic activity ratio may be desired will be apparent to those of skill in the art.

Decreasing activity in at least a portion of the sympathetic system may be employed where there is a normal or an abnormally low parasympathetic function and/or abnormally high sympathetic function. Such may also be desired in instances where, prior to decreasing sympathetic function in, e.g., at least one parasympathetic nerve fiber, parasympathetic activity is higher than the sympathetic activity, but the differential between the two needs to be increased further. For example, such instances may occur where a subject has normal or above normal (i.e., abnormally high) sympathetic function, but also has elevated parasympathetic function (i.e., abnormally high), e.g., a relative bias towards parasympathetic function may be present. Other instances include normal or below normal (i.e., abnormally low) sympathetic activity and/or normal or above normal (i.e., abnormally high) parasympathetic activity. The above-described examples of instances where decreasing sympathetic activity may be desired is exemplary only and is in no way intended to limit the scope of the invention and other instances where decreasing sympathetic activity to provide an increase in the parasympathetic activity/sympathetic activity ratio may be desired will be apparent to those of skill in the art.

One way of inhibiting activity in at least a portion of the autonomic nervous system is by the application of a nerve block. Application of a nerve block at least partially prevents nerve transmission across the location of the block. A nerve block can be administered to modulate autonomic function using all the methods and devices described herein including pharmacological and/or electrical means. As noted above, in certain embodiments, activity in at least a portion of the autonomic nervous system may be increased and activity in at least a portion of the autonomic nervous system may be decreased. For example, in certain embodiments, activity in at least a portion of the sympathetic system may be increased and activity in at least a portion of the parasympathetic system may be inhibited, e.g., to decrease the parasympathetic activity/sympathetic activity ratio. In other embodiments, activity in at least a portion of the parasympathetic system may be increased and activity in at least a portion of the sympathetic system may be inhibited, e.g., to decrease the parasympathetic activity/sympathetic activity ratio. As described above, any portion of the parasympathetic and/or sympathetic nervous systems may be modulated to increase activity and activity in any portion of the ANS may be inhibited to provide the desired ratio of parasympathetic activity to sympathetic activity. Such a protocol may be employed, e.g., in instances where sympathetic function is normal or abnormally low and/or parasympathetic function is normal or abnormally high, or where parasympathetic function is normal or abnormally low and/or sympathetic function is normal or abnormally high, where normal is determined by the typical or average autonomic nervous system functions for a healthy subject, e.g., a healthy human subject ranging in age from about 20 years old to about 25 years old.

Embodiments wherein activity in at least a portion of the autonomic nervous system may be increased and activity in at least a portion of the autonomic nervous system may be decreased may be employed to alter the dominance and/or may be employed to modulate the differential between the two systems. For example, prior to modulating the autonomic system according to the subject invention, the activity in the parasympathetic system may be higher than activity in the sympathetic system and the subject methods may be employed to increase the sympathetic activity to a level that is greater than the parasympathetic activity and/or may be employed to alter the differential or difference in activity levels of the two systems such as decreasing the difference in activity levels or increasing the difference in activity levels.

Increasing activity in at least a portion of the autonomic nervous system, e.g., increasing activity in at least a portion of the parasympathetic system, and decreasing activity in at least a portion of the autonomic nervous system, e.g., decreasing activity in at least a portion of the sympathetic system, may be performed simultaneously or sequentially such that at least a portion of the autonomic nervous system, e.g., at least a portion of the parasympathetic nervous system, may be pharmacologically and/or electrically modulated to increase activity therein prior or subsequent to inhibiting activity in at least a portion of the autonomic nervous system e.g., at least a portion of the sympathetic nervous system, such as by electrical and/or pharmacological means.

Regardless of whether increasing activity in at least a portion of the autonomic nervous system, e.g., in at least a portion of the parasympathetic system, and decreasing activity in at least a portion of the autonomic nervous system, e.g., in at least a portion of the sympathetic system, is performed simultaneously or sequentially, the parameters for increasing activity in at least a portion of autonomic nervous system and decreasing activity in at least a portion of the autonomic nervous system may be analogous to that described above.

Modulation of the autonomic nervous system may be accomplished using any suitable method, including employing electrical, thermal, vibrational, magnetic, acoustic, baropressure, optical, or other sources of energy to modulate autonomic balance, where in representative embodiments modulation is achieved via pharmacological modulation and/or electrical energy modulation in a manner that is effective to treat a subject for a food allergy syndrome condition.

Certain embodiments include pharmacologically or electrically stimulating a portion of the subject's nervous system in a manner that causes a modulation of at least a portion of a subject's autonomic nervous system, e.g., by increasing parasympathetic activity and/or decreasing sympathetic activity or by increasing sympathetic activity and/or decreasing parasympathetic activity in at least a portion of the subject's autonomic nervous system. In certain embodiments, modulation may include increasing the sympathetic activity/parasympathetic activity ratio in at least a portion of the subject's autonomic nervous system. In certain embodiments, a combination of electrical and pharmacological may be employed.

Pharmacologic Modulation

In certain embodiments of the subject methods, the therapy comprises a pharmacological modulation, which modulation may result in modulation of the ANS and/or some other system of the subject in manner effective to modulate the dynamic measure of homeostatic capacity, as desired. By "pharmacologically modulation" is meant altering or changing one or more systems of the subject by pharmacological means to provide a desired change, alteration or shift in system(s) function. In embodiments in which pharmacological agent is administered, any suitable protocol may be used, where certain protocols include using an pharmacological agent administering device to deliver a suitable amount of pharmacological agent to a subject. Methods and corresponding devices and systems for applying at least one pharmacological agent to a subject and which may be adapted for use in the subject invention are described, e.g., in U.S. Pat. Nos. 7,363,076; 7,149,574, 7,738,952; 7,899,527; 7,676,269; 8,121,690; 8,569,277; 8,909,340 United States Published Application Nos. 20050143378; 20100260669; 20110015188; 20100119482; 20110256097; 20060206149; 20140065129; 20140369969 and U.S. patent application Ser. No. 14/737,248; the disclosures of which are herein incorporated by reference.

Any convenient pharmacological agent may be employed. Pro-sympathetic agents of interest include, but are not limited to: beta agonists, e.g., dobutamine, metaproterenol, terbutaline, ritodrine, albuterol; alpha agonists, e.g., selective alpha 1-adrenergic blocking agents such as phenylephrine, metaraminol, methoxamine; prednisone and steroids, (e.g., available under the brand names CORATN, DELTASONE, LIQUID PRED, MEDICORTEN, ORASONE, PANASOL-S, PREDNICEN-M, PREDNISONE INTENSOL); indirect agents that include norepinephrine, e.g., ephedrine, ampthetamines, phenylpropanolamines, cyclopentamines, tuaminoheptanes, naphazolines, tetrahydrozolines; epinephrine; norepinephrine; acetylcholine; sodium; calcium; angiotensin I; angiotensin II; angiotensin converting enzyme I ("ACE I"); angiotensin converting enzyme II ("ACE II"); aldosterone; potassium channel blockers and magnesium channel blockers, e.g., valproate (sodium valproate, valproic acid), lithium; cocaine; amphetamines; terbutaline; dopamine; doputamine; antidiuretic hormone ("ADH") (also known as vasopressin); oxytocin (including PITOCINE); THC cannabinoids; and combinations thereof.

Pro-parasympathetic agents of interest include, but are not limited to: Beta Blockers, Aldosterone Antagonists; Angiotensin II Receptor Blockers; Angiotensin Converting Enzyme Inhibitors; Statins; Triglyceride Lowering Agents; Insulin Sensitizers; Insulin Secretagogues; Insulin Analogs; Alpha-glucosidase Inhibitors; SGLT2 Inhibitors; Immunomodulators, including agents that bind/react to CD4, gp39, B7, CD19, CD20, CD22, CD401, CD40, CD40L and CD23 antigens; Sympathomimetics; Cholinergics; Calcium Channel Blockers; Sodium Channel Blockers; Glucocorticoid Receptor Blockers; Peripheral Adrenergic Inhibitors; Blood Vessel Dilators; Central Adrenergic Agonists; Alpha-adrenergic Blockers; Combination Diuretics; Potassium-sparing Diuretics; Nitrate Pathway Modulators; Cyclic Nucleotide Monophosphodiesterase (PDE) Inhibitors; Vasopressin Inhibitors; Renin Inhibitors; Estrogen and Estrogen Analogues and Metabolites; Vesicular Monoamine Transport (VMAT) Inhibitors; Progesterone Inhibitors; Testosterone Inhibitors; Gonadotropin-releasing Hormone Inhibitors; Dipeptidyl Peptidase IV inhibitors; Anticoagulants; Thrombolytics.

Pharmaceutical agents of interest also include biotherapeutic agents. Biotherapeutic agents include, but are not limited to: nucleic acid agents, polypeptide agents, complex biological preparations, e.g., blood products and derivatives thereof, e.g., plasma, mitochondrial preparations (e.g., for mitochondrial transfer); etc.

In some instances, the agent modulates the activity of the protein following expression, such that the agent is one that changes the activity of the protein encoded by a target gene following expression of the protein from the target gene. In these instances, the agent is one that may act directly with protein encoded by the target gene.

In yet other embodiments, the agent modulates expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of a functional target protein. Inhibition of protein expression may be accomplished using any convenient means, including use of an agent that inhibits protein expression, such as, but not limited to: antisense agents, RNAi agents, agents that interfere with transcription factor binding to a promoter sequence of the target gene, or inactivation of the target gene, e.g., through recombinant techniques, etc.

For example, antisense molecules can be used to downregulate expression of a target gene in the cell. The antisense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In addition, the transcription level of a target protein can be regulated by gene silencing using RNAi agents, e.g., double-strand RNA (Sharp (1999) *Genes and Development* 13: 139-141). RNAi, such as double-stranded RNA interference (dsRNAi) or small interfering RNA (siRNA), has been extensively documented in the nematode *C. elegans* (Fire, A., et al, *Nature,* 391, 806-811, 1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enables one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

In another embodiment, the target gene is inactivated so that it no longer expresses a functional protein. By inactivated is meant that the gene, e.g., coding sequence and/or regulatory elements thereof, is genetically modified so that it no longer expresses a functional target protein. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998, 144; 5,948,653; 5,925,544; 5,830,698; 5,780,296; 5,776, 744; 5,721,367; 5,614,396; 5,612,205; the disclosures of which are herein incorporated by reference.

Also of interest in certain embodiments are dominant negative mutants of target proteins, where expression of such mutants in the cell result in a modulation, e.g., decrease, in target protein activity. Dominant negative mutants are mutant proteins that exhibit dominant negative target protein activity. As used herein, the term "dominant negative activity" refers to the inhibition, negation, or diminution of certain particular activities of a target protein, such as the apoptotic activity of a target protein. Dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz (1987) Nature 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In yet other embodiments, the agent is an agent that modulates, e.g., inhibits, target protein activity by binding to the target protein and/or inhibiting binding of target protein to a second protein. For example, small molecules that bind to a target protein and inhibit its activity are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In yet other instances, the agent is an agent that increases the activity of a protein, e.g., by increasing the amount of protein, e.g., in a cell. For example, introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; encode a dominant negative mutation, or dominant or constitutively active mutations of native sequences; altered regulatory sequences, etc.

A variety of methods can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655-3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-X™ expression system from Clontech (Clontechniques (January 2000) p. 10-12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:516-544).

In representative embodiments, methods are used that achieve a high efficiency of transfection, and therefore circumvent the need for using selectable markers. These may include adenovirus infection (see, for example Wrighton, 1996, J. Exp. Med. 183: 1013; Soares, J. Immunol., 1998, 161: 4572; Spiecker, 2000, J. Immunol 164: 3316; and Weber, 1999, Blood 93: 3685); and lentivirus infection (for example, International Patent Application WO000600; or WO9851810). Adenovirus-mediated gene transduction of endothelial cells has been reported with 100% efficiency. Retroviral vectors also can have a high efficiency of infection with endothelial cells, with reported infection efficiencies of 40-77%. Other vectors of interest include lentiviral vectors, for examples, see Barry et al. (2000) Hum Gene Ther 11(2):323-32; and Wang et al. (2000) Gene Ther 7(3):196-200.

Viral vectors include retroviral vectors (e.g. derived from MoMLV, MSCV, SFFV, MPSV, SNV etc), lentiviral vectors (e.g. derived from HIV-1, HIV-2, SIV, BIV, FIV etc.), adeno-associated virus (AAV) vectors, adenoviral vectors (e.g. derived from Ad5 virus), SV40-based vectors, Herpes Simplex Virus (HSV)-based vectors etc. A vector construct may include drug resistance genes (neo, dhfr, hprt, gpt, bleo, puro etc) enzymes (β-galactosidase, alkaline phosphatase etc) fluorescent genes (e.g. GFP, RFP, BFP, YFP) or surface markers (e.g. CD24, NGFr, Lyt-2 etc).

The gene or protein may be introduced into tissues or host cells by any number of routes, including viral infection, microinjection, or fusion of vesicles. Jet injection may also be used for intra-muscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Once the gene corresponding to a selected polynucleotide is identified, its expression can be regulated in the cell to which the gene is native. For example, an endogenous gene of a cell can be regulated by an exogenous regulatory sequence as disclosed in U.S. Pat. No. 5,641,670; the disclosure of which is herein incorporated by reference.

Also of interest in these embodiments is the administration of a target protein itself or active fragments, as well as mimetics, thereof.

In some instances, the active agent is configured to cross the blood brain barrier. For example, the active agent may be conjugated to a moiety that confers upon the active agent the ability to cross the blood brain barrier. Such a configuration allows for the targeting of the active agent to tissues within the blood brain barrier. In some embodiments the subject moiety may be a peptide, e.g., a cell-penetrating peptide. Suitable peptides that facilitate crossing of the blood brain barrier include, but are not limited to positively charged peptides with amphipathic characteristics, such as MAP, pAntp, Transportan, SBP, FBP, TAT$_{48-60}$, SynB1, SynB3 and the like.

In other embodiments, the subject moiety may be a polymer. Suitable polymers that facilitate crossing of the blood brain barrier include, but are not limited to, surfactants such as polysorbate (e.g., Tween® 20, 40, 60 and 80); poloxamers such as Pluronic® F 68; and the like. In some embodiments, an active agent is conjugated to a polysorbate such as, e.g., Tween® 80 (which is Polyoxyethylene-80-sorbitan monooleate), Tween® 40 (which is Polyoxyethylene sorbitan monopalmitate); Tween® 60 (which is Poly-oxyethylene sorbitan monostearate); Tween® 20 (which is Polyoxyethylene-20-sorbitan monolaurate); polyoxyethylene 20 sorbitan monopalmitate; polyoxyethylene 20 sorbitan monostearate; polyoxyethylene 20 sorbitan monooleate; etc. Also suitable for use are water soluble polymers, including, e.g.: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and poly-vinyl alcohol ("PVA"); poly(vinyl pyrrolidinone) ("PVP"); poly(amino acids); dextran, and proteins such as albumin. Block co-polymers are suitable for use, e.g., a polyethylene oxide-polypropylene oxide-polyethylene-oxide (PEO-PPO-PEO) triblock co-polymer (e.g., Pluronic® F68); and the like; see, e.g., U.S. Pat. No. 6,923,986. Other methods for crossing the blood brain barrier are discussed in various publications, including, e.g., Chen & Liu (2012) Advanced Drug Delivery Reviews 64:640-665.

The targeting moiety may be attached to the subject active agent via any convenient method. The targeting moiety may be attached to the active agent via a single bond or a suitable linker, e.g., a PEG linker, a peptidic linker including one or more amino acids, or a saturated hydrocarbon linker. A variety of linkers find use in the subject modified compounds.

In certain embodiments where targeting moieties or active agents are small molecule compounds, such compounds may contain, or be modified to contain, an α-nucleophilic group that serves as a reactive partner useful in conjugation to a compound disclosed herein. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

In certain embodiments where targeting moieties or active agents are peptides, any convenient reagents and methods may be used to conjugate the targeting moiety and subject active agent, for example, conjugation methods as described in G. T. Hermanson, "Bioconjugate Techniques" Academic Press, 2nd Ed., 2008, solid phase peptide synthesis methods, or fusion protein expression methods. Reactive functional groups for conjugation of peptidic compounds, via an optional linker, include, but are not limited to: an azido group, an alkynyl group, a phosphine group, a cysteine residue, a C-terminal thioester, aryl azides, maleimides, carbodiimides, N-hydroxysuccinimide (NHS)-esters, hydrazides, PFP-esters, hydroxymethyl phosphines, psoralens, imidoesters, pyridyl disulfides, isocyanates, aminooxy-, aldehyde, keto, chloroacetyl, bromoacetyl, and vinyl sulfones.

Other variations of standard peptide coupling chemistry may be employed. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphosphate), DPPA (diphenylphosphorazidate), BOP (benzotriazol-1-yloxytris(dimethylamino)phosphonium hexafluorophosphate), HBTU (0-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate).

In certain embodiments where targeting moieties or active agents are oligonucleotides, any convenient reagents and methods may be used to conjugate the targeting moiety and subject active agent. For example conjugation methods described in P. Herdewijn, "Oligonucleotide Synthesis" Humana Press, 2005, such as total stepwise solid-phase synthesis methods, or methods utilizing incorporation of 2'-aldehydes for use in ligation via hydrazine, oxime, or thiazolidine linkages. In other cases, the oligonucleotide may be first conjugated, by methods well known in the art, to a natural or synthetic amino acid such that functional groups on the amino acid may be utilized for conjugation by any of the relevant peptide conjugation methods described herein.

In another embodiment where the targeting moiety is an antibody, the antibody may include a light chain polypeptide including a C-terminal amino acid extension, which extension includes a cysteine residue, where the agent is conjugated to the cysteine residue (directly or indirectly (e.g., via a linker)) of the C-terminal amino acid extension. In one embodiment, conjugation method involves the preferential (or "biased") conjugation of agent to the cysteine residue of the C-terminal amino acid extension over a cysteine residue outside the C-terminal extension. In certain aspects, the conjugation includes conjugating a linker to a sulfhydryl group of the cysteine residue, e.g., using maleimide reaction chemistry, haloacetyl reaction chemistry, pyridyl disulfide reaction chemistry, or any other suitable reaction chemistry as described elsewhere herein. The methods of making the conjugate may further include reducing the sulfhydryl group of the cysteine residue prior to the conjugating step, e.g., using a suitable reducing agent and reaction conditions as described above. An alternative embodiment of the present disclosure does not require a reduction step as the cysteine within the light chain extension is already in a reduced state as a synthesis product.

In certain aspects, the agent is linked to the cysteine of the C-terminal extension using maleimide reaction chemistry. The maleimide group reacts specifically with sulfhydryl groups when the pH of the reaction mixture is between pH 6.5 and 7.5; the result is formation of a stable thioether linkage. In more alkaline conditions (pH>8.5), primary amines compete with thiols for reaction with maleimides, and also increases the rate of hydrolysis of the maleimide group to a non-reactive maleamic acid. Maleimides do not react with tyrosines, histidines or methionines. Bioconjugation approaches that employ maleimide-based linkers are known and described in detail, e.g., in Hermanson, G. T., Bioconjugate Techniques, 2nd ed. San Diego, Calif. Academic Press 2008; Aslam & Dent, Bioconjugation: Protein Coupling Techniques for the Biomedical Sciences, London Macmillan Reference Ltd 1998; Kalia & Raines, Advances in Bioconjugation, Curr. Org. Chem. 14(2):138-147; and elsewhere.

According to certain embodiments, the agent is linked to the cysteine of the C-terminal extension using haloacetyl reaction chemistry. In certain aspects, a haloacetyl crosslinker that includes an iodoacetyl or a bromoacetyl group is employed. Haloacetyls react with sulfhydryl groups at physiologic pH. The reaction of the iodoacetyl group proceeds by nucleophilic substitution of iodine with a sulfur atom from a sulfhydryl group, resulting in a stable thioether linkage.

In certain aspects, the agent is linked to the cysteine of the C-terminal extension using pyridyl disulfide reaction chemistry. Pyridyl disulfides react with sulfhydryl groups over a broad pH range (with pH 4 to 5 being optimal) to form disulfide bonds. During the reaction, a disulfide exchange occurs between the molecule's —SH group and the reagent's 2-pyridyldithiol group. As a result, pyridine-2-thione is released and can be measured spectrophotometrically (Amax=343 nm) to monitor the progress of the reaction.

To generate a reduced sulfhydryl in the cysteine of the C-terminal amino acid extension to which the agent may be attached (e.g., via a linker), the sulfhydryl group of the cysteine may be contacted with a suitable reducing agent under conditions sufficient to reduce the sulfhydryl group. In certain aspects, the reducing agent is selected from cysteamine hydrochloride, 2-mercaptoethanol, dithiothreitol (DTT), 2-mercaptoethylamine, tris(2-carboxyl)phosphine (TCEP), cysteine HCl, N-ethylmaleimide, Nacystelyn, dornase alfa, thymosin 134, guaifenesin TCEP HCl, and any combination thereof. Reaction conditions for such reducing agents are known in the art and may be optimized, e.g., to promote selectivity or "bias" the reduction of the sulfhydryl group of the cysteine(s) present in the C-terminal extension as opposed to the cysteine residues present in the parental antibody (e.g., the cysteine residues that participate in disulfide bonding between CL and CH1 of the light and heavy chains, and/or between the hinge regions of the heavy chains). An alternative embodiment of the invention does not require a reduction step as the cysteine within the light chain extension is already in a reduced state as a synthesis product.

Preferential reduction of the cysteine(s) of the C-terminal amino acid extension over one or more cysteine residues outside the C-terminal amino acid extension (or exclusive reduction of the cysteine(s) of the C-terminal amino acid extension) may be achieved by selection of suitable reduction conditions. In certain aspects, suitable reduction conditions include suitable selection of one or more of the following: a mild reducing agent and/or a reducing agent having a steric bulk that confers upon the reducing agent a preference for reducing a cysteine of the C-terminal amino acid extension; concentrations of the reducing agent and substrate; the temperature at which the reduction reaction is carried out, the pH of the reduction reaction mixture; the buffer used in the reduction reaction; and/or conditions under which the cells expressing the extended C-terminal light chain polypeptides are cultured (e.g., to obtain free thiol on the C-terminal extension and/or to generate readily reduced intermolecular disulfides). The agent conjugated to the antibody may be any useful agent described elsewhere herein. In certain aspects where the agent is an antibody, the agent may be conjugated to a targeting moiety by antibody conjugation methods described herein.

The ordinarily skilled artisan will appreciate that factors such as pH and steric hindrance (i.e., the accessibility of the amino acid residue to reaction with a reactive partner of interest) are of importance. Modifying reaction conditions to provide for optimal conjugation conditions is well within the skill of the ordinary artisan, and is routine in the art.

In practicing methods according to embodiments of the invention, an effective amount of the active agent is provided in the target cell or cells. In some instances, the effective amount of the modulatory agent is provided in the cell by contacting the cell with the modulatory agent. Contact of the cell with the modulatory agent may occur using any convenient protocol. The protocol may provide for in vitro or in vivo contact of the modulatory agent with the target cell, depending on the location of the target cell. Contact may or may not include entry of the agent into the cell. For example, where the target cell is an isolated cell and the modulatory agent is an agent that modulates expression of target protein, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the modulatory agent, and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the modulatory agent may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body.

In the subject methods, the active agent(s) may be administered to the targeted cells using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

Electrical Modulation

In certain embodiments, to accomplish the desired modulation of the subject dynamic measure of homeostatic capacity, electrical energy (electrical modulation) may be applied to at least a portion of a subject, where such electrical energy may be excitatory or inhibitory and in certain embodiments may include both excitatory and inhibitory stimulation. By "electrically modulating" is meant altering or changing at least a portion of the subject by electrical means to provide a change, alteration or shift in at least one component or aspect of an electrical system of the subject.

Any suitable area may be targeted for electrical modulation. Areas that may be targeted include, but are not limited to, pre- and post-ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency. In certain embodiments, electrical energy is applied using any of the devices described below.

A number of different methods and corresponding devices and systems for applying electrical energy to a subject and which may be adapted for use in the subject invention are described, e.g., in U.S. Pat. Nos.: in U.S. Pat. Nos. 7,363,076; 7,149,574, 7,738,952; 7,899,527; 7,676,269; 8,121,690; 8,569,277; 8,909,340 United States Published Application Nos. 20050143378; 20100260669; 20110015188; 20100119482; 20110256097; 20060206149; 20140065129; 20140369969 and U.S. patent application Ser. No. 14/737,248; the disclosures of which are herein incorporated by reference.

Paradoxical Modulation

In some instances, the methods include employing a paradoxical protocol in order to obtain a desired modulation in the dynamic measure of homeostatic capacity. In some of these embodiments, a counter-intuitive stimulus is applied to the subject in a manner effective to cause the subject to mount a compensatory response effective to ultimately modulate the dynamic homeostatic capacity of the subject, as desired. In practicing methods according to such embodiments, a stimulus is applied to the subject, where the stimulus is of a nature and magnitude sufficient to achieve the desired modulation. In certain embodiments, the applied stimulus is one of short duration, where by short duration is meant that the applied stimulus lasts for 1 week or less, e.g., 3 days or less, e.g., 1 day or less, e.g., 12 hours or less, 5 hours or less, 1 hour or less, 30 min or less, 15 min or less, 5 min or less, 1 min or less, 30 s or less, 1 s or less, where the duration of the applied stimulus may be even shorter. In certain embodiments, the applied stimulus is one of long duration, where by long duration is meant that the applied stimulus lasts for 1 week or longer, e.g., 2 weeks or longer, 1 month or longer, 2 months or longer, 3 months or longer, or 6 months or longer, where the duration of the applied stimulus may be even shorter. Where the stimulus is a pharmacological stimulus, the duration refers to the period in which the pharmacological agent from an administered dosage is active. Where the stimulus is an electrical stimulus, the duration refers to the total of electrical applications received by a subject over a given period, analogous to a dose of a pharmacological agent.

Following administration, the stimulus is removed, e.g., by metabolization of the pharmacological agent or cessation of application of electrical energy, and the subject is permitted to mount a compensatory response. In this following period, no additional stimulus is administered to the subject. The duration of this period between stimulus application, which may be referred to as a "holiday" period, may vary, but in representative embodiments is 1 second or longer, such as 30 seconds or longer, e.g., 1 minute or longer, 5 minutes or longer, 10 minutes or longer, 15 minutes or longer, 30 minutes or longer, 1 hour or longer, 6 hours or longer, 12 hours or longer, 1 day or longer, such as 2 days or longer, including 5 days or longer, 10 days or longer, e.g., 15 days or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied stimulus may vary, where in certain embodiments the stimulus may be a pharmacological stimulus and/or an electrical stimulus. As such, in certain embodiments, the stimulus is a pharmacological stimulus. In other embodiments, the stimulus is an electrical stimulus. In yet other embodiments, the stimulus is a combination of pharmacological and electrical stimuli. Accordingly, in certain embodiments, the enhancing is by administering a pharmacological agent to the subject. In yet other embodiments, the enhancing is by electrical stimulation, e.g., by employing an implanted electrical energy application device.

Further details regarding paradoxical therapies that may be employed in embodiments of the methods include those described in U.S. Pat. Nos. 8,691,877 and 8,571,650, the disclosures of which are herein incorporated by reference.

Pulsatile Therapy

In some instances, the methods include employing a pulsatile protocol in order to obtain a desired modulation in the dynamic measure of homeostatic capacity. In some of these embodiments, a stimulus is applied in a pulsatile manner to the subject effective to cause the desired modulation in homeostatic capacity. Pulsatile protocols may be employed to enhance homeostatic capacity and aspects thereof, e.g., dynamic range, robustness, etc. In pulsatile stimulation protocols, intermittent stressors may be employed, e.g., in the form of iterative stress and rest and/or variation (irregularity or regularity) and intermittency of stressor, e.g., in order to enhance homeostatic capacity. A dynamic range of stressors may be employed to increase the dynamic range of homeostatic capacity and/or to strengthen homeostatic capacity.

In practicing methods according to such embodiments, a pulsatile stimulus is applied to the subject, where the pulsatile stimulus is of a nature and magnitude sufficient to achieve the desired modulation. In certain embodiments, the applied pulsatile stimulus is one of short duration, where by short duration is meant that the applied stimulus lasts for 1 week or less, e.g., 3 days or less, e.g., 1 day or less, e.g., 12 hours or less, 5 hours or less, 1 hour or less, 30 min or less, 15 min or less, 5 min or less, 1 min or less, 30 s or less, 1 s or less, where the duration of the applied stimulus may be even shorter. In certain embodiments, the applied pulsatile stimulus is one of long duration, where by long duration is meant that the applied stimulus lasts for 1 week or longer, e.g., 2 weeks or longer, 1 month or longer, 2 months or longer, 3 months or longer, or 6 months or longer, where the duration of the applied stimulus may be even shorter. Where the pulsatile stimulus is a pharmacological stimulus, the duration refers to the period in which the pharmacological agent from an administered dosage is active. Where the pulsatile stimulus is an electrical stimulus, the duration refers to the total of electrical applications received by a subject over a given period, analogous to a dose of a pharmacological agent.

Following administration of a given stimulation in a pulsatile stimulus protocol, there is a non-stimulation period. The duration of this non-stimulation period between stimuli application, which may be referred to as a "holiday" period, may vary, but in certain embodiments is 1 second or longer, such as 30 seconds or longer, e.g., 1 minute or longer, 5 minutes or longer, 10 minutes or longer, 15 minutes or longer, 30 minutes or longer, 1 hour or longer, 6 hours or longer, 12 hours or longer, 1 day or longer, such as 2 days or longer, including 5 days or longer, 10 days or longer, e.g., 15 days or longer.

In certain embodiments, pulsatile stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied pulsatile stimulus may vary, where in certain embodiments the pulsatile stimulus may be a pharmacological stimulus and/or an electrical stimulus. As such, in certain embodiments, the stimulus is a pharmacological stimulus. In other embodiments, the stimulus is an electrical stimulus. In yet other embodiments, the stimulus is a combination of pharmacological and electrical stimuli. Accordingly, in certain embodiments, the enhancing is by administering a pharmacological agent to the subject. In yet other embodiments, the enhancing is by electrical stimulation, e.g., by employing an implanted electrical energy application device.

Behavioral Therapy

In some embodiments, the therapy that is administered to the subject is a behavioral therapy. By "behavioral therapy" is meant at protocol or regimen that results in a change in the behavior, i.e., the way that the subject acts, in a manner sufficient to modulate the dynamic measure of homeostatic capacity and treat the subject for the target condition. Behavioral therapies that may be employed may vary, where examples of such therapies include, but are not limited to: exercise regimens (e.g., cardiovascular, weight lifting, stretching, yoga); resting/sleeping regimens (e.g., meditation); physical therapies; psychological therapies, e.g., counseling for enhancement of emotions/mood; substance abuse therapies, e.g., smoking cessation therapies, alcohol abstinence therapies; drugs of abuse abstinence therapies, etc. Behavioral therapies may vary in terms of application, where examples include but are not limited to those that are administered via professional and/or consumer devices/services, e.g., mobile apps, videos, computers, etc.

Dietary Therapy

In some embodiments, the therapy that is administered to the subject is a dietary therapy. By "dietary therapy" is meant at protocol or regimen that results in a change in the nutritional and/or chemical intake of the subject, e.g., the types of foods/liquids that the subject ingests or otherwise introduces into the body, in a manner sufficient to modulate the dynamic measure of homeostatic capacity and treat the subject for the target condition. Dietary therapies that may be employed may vary, where examples of such therapies include, but are not limited to: low carbohydrate diets, low fat diets, low calorie diets, vegetarian diets, organic diets, etc.; nutritional supplement regimens, e.g., vitamin regimens; etc.

Environment Therapy

In some embodiments, the therapy that is administered to the subject is an environmental therapy. By "environmental therapy" is meant at protocol or regimen that results in a change in the contextual environment of the subject, e.g., the perceived surroundings of the subject, in a manner sufficient to modulate the dynamic measure of homeostatic capacity and treat the subject for the target condition. Environmental therapies that may be employed may vary, where examples of such therapies include, but are not limited to: changes in day/night duration; changes in geographic locations, e.g., to obtain a desired temperature and/or elevation, etc.

Surgical Therapy

In some embodiments, the therapy that is administered to the subject is a surgical therapy. By "surgical therapy" is meant a manual or operative procedure on a living subject. Surgical procedures may vary widely, and may or may not be minimally invasive, as is known in the art.

Modulation of Dynamic Measure of Homeostatic Capacity

As summarized above, the therapy is administered to the subject (e.g., by a health practitioner and/or the subject itself, depending the nature of the particular therapy) in a manner sufficient to modulate the subject's dynamic measure of homeostatic capacity to more closely approximate a target dynamic measure of homeostatic capacity and treat the subject for the condition. In some embodiments, the methods result in an enhancement or an increase in the dynamic measure of the homeostatic capacity of the subject. The magnitude of the enhancement/increase may vary, where in some instances the magnitude is 2-fold or greater, such as 5-fold or greater, e.g., 10-fold or greater.

In some embodiments, the methods may result in at least partially restoring the dynamic measure of homeostatic capacity of the subject. By "at least partially restoring the homeostatic capacity of the subject" is meant that the homeostatic capacity of the subject is restored to be normal, e.g., in those embodiments were normal is the target dynamic measure. By "normal" is meant the dynamic measure of homeostatic capacity of a healthy subject of a particular age. In certain embodiments, the healthy subject is a healthy human at an age after puberty, e.g., 18 year old, 19 year old, 20 year old, 21 year old, 22 year old, 23 year old, 24 year old, 25 year old, 26 year old, 27 year old, 28 year old, 29 year old, 30 year old, 31 year old, 32 year old, 33 year old 34 year old, 35 year old, 36 year old, 37 year old, 38 year old, 39 year old, 40 year old, 41 year old, 42 year old, 43 year old, 44 year old, 45 year old, 46 year old, 47 year old, 48 year old, 49 year old or 50 year old. In some instances, the normal function with respect to homeostatic capacity is that of a healthy human 25 year old. In some instances, the dynamic measure is enhanced to a target dynamic measure that is greater than that observed in a normal subject, e.g., a super normal value. In these instances, the magnitude by which the target dynamic measure may exceed the normal measure may vary, such as by 2-fold or greater, e.g., 5-fold or greater, including 10-fold or greater.

As indicated above, the therapies are applied such that the dynamic measure of homeostatic capacity more closely approximates a target dynamic measure, e.g., the normal measure or super normal measure, such as described above. By "approximates" is meant, in some instances, that the dynamic measure of homeostatic capacity is changed by the therapy to be 50% or more, e.g., 75% or more of the target function, such as 80% or more of the target dynamic measure, including 90% or more of the target function, e.g., 95% or more of the target function, including 99% or more of the target dynamic measure.

Therapeutic methods as described herein may further include, following application of therapy, assessing dynamic homeostatic capacity to determine with the measure approximates the target measure, as desired. In such embodiments, the subject's dynamic measure of homeostatic capacity may be made using any convenient protocol, such as that described above.

Devices and Systems

A number of different devices and systems may be employed in accordance with the subject invention. Devices and systems that may be adapted or configured for use in the subject invention include devices and systems for obtaining dynamic biometric data from a subject and optionally further processing the obtained data in some, e.g., e.g., in making a homeostatic capacity evaluation of the subject based on the obtained dynamic biometric data, in making a dynamic diagnosis based on the obtained dynamic biometric data, etc. In some instances, the device may be configured to also output a therapeutic treatment regimen recommendation based on the homeostatic capacity evaluation and/or provide such a therapeutic treatment to the subject.

Devices of interest may include one or more functional modules, which may be distributed among two or more distinct hardware units or integrated into a single hardware unit, e.g., as described in greater detail below. In some instances, the devices include a dynamic biometric data obtainment module, a homeostatic capacity evaluation module, and a homeostatic capacity evaluation output module. The dynamic biometric obtainment module is adapted to obtain dynamic biometric data, e.g., by being in operational communication with one or more biometric parameter sensors and or an input configured to receive dynamic biometric data from a source of such data, and transmit the obtained biometric data to the process unit module. The homeostatic capacity evaluation module is adapted to retrieve the dynamic biometric data from the dynamic biometric data obtainment module and make a homeostatic capacity evaluation therefrom. As such, the module is configured to produce a homeostatic capacity evaluation from the received or input dynamic biometric data. In some instances, the systems further include a therapeutic treatment regimen module, which is configured to identify a suitable therapeutic regimen based on the homeostatic capacity evaluation. The output module is adapted to provide the homeostatic capacity evaluation (and in some instances a therapeutic treatment regimen) to a user, e.g., the subject or interested stakeholder. In some instances, the output module is configured to display the homeostatic capacity evaluation to a user, e.g., via graphical user interface (GUI). In one embodiment, a visual display can be used for displaying the homeostatic capacity evaluation. Other outputs may also be employed, e.g., printouts, messages (e.g., text messages or emails) sent to another display device, to a storage location for later viewing (e.g., the cloud), etc.

One embodiment of a device for evaluating a subject's homeostatic capacity is configured as follows. A dynamic biometric obtainment module is configured to obtain subject's dynamic biometric data. This biometric data from the subject may then be input into a homeostatic capacity evaluation module, along with biometric data from a database, which contains data made up from individuals of a variety of different ages and health of known homeostatic capacities. The homeostatic capacity evaluation module evaluates the subject's homeostatic capacity based on the biometric data from the subject and from the database using a classification rule derived from a machine learning algorithm, which may be any convenient algorithm, such as but not limited to: Fisher's linear discriminant, logistic regression, naïve Bayes classifier, quadratic classifiers, k-nearest neighbor, decision trees, neural networks, and support vector machine. The homeostatic capacity evaluation module may then output the subject's predicted homeostatic capacity in a user-readable format via a homeostatic capacity evaluation output module.

An example of a device according to an embodiment of the invention as described above is illustrated in the flow chart of FIG. 1. Dynamic biometric obtainment module 100 is adapted to obtain subject's dynamic biometric data 110. This biometric data 110 from the subject is then input into the homeostatic capacity evaluation module 140, along with biometric data 130 from a database 120. The database 120 contains data made up from individuals of a variety of different ages and health of known homeostatic capacities. The homeostatic capacity evaluation module 140 evaluates the subject's homeostatic capacity based on the biometric data from the subject 110 and from the database 130 using a classification rule derived from a machine learning algorithm, which may be any convenient algorithm, such as but not limited to: Fisher's linear discriminant, logistic regression, naïve Bayes classifier, quadratic classifiers, k-nearest neighbor, decision trees, neural networks, and support vector machine. The homeostatic capacity evaluation output module 150 then provides the homeostatic capacity evaluation to the user.

Figure 2:
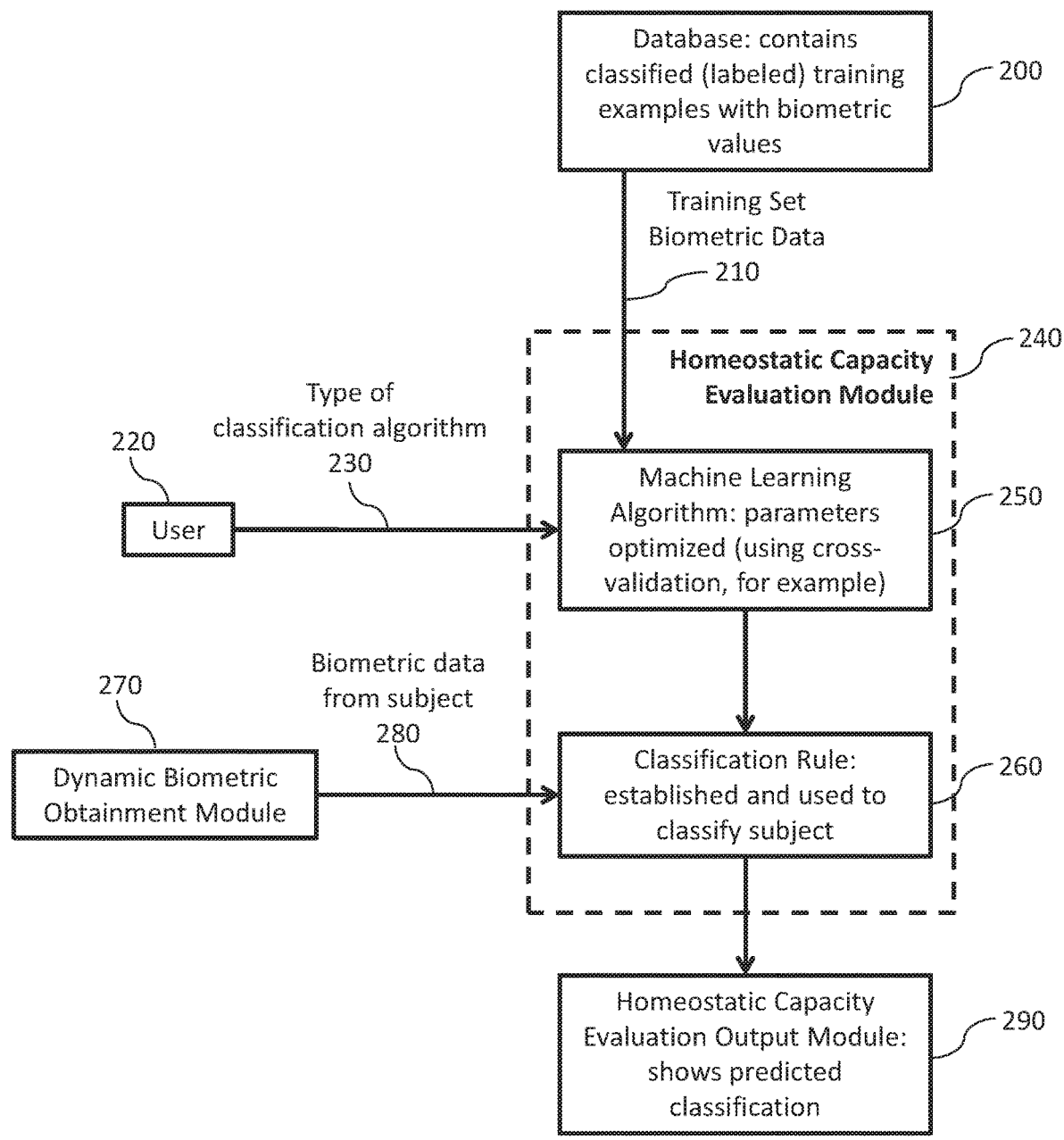
FIG. 2 is a flow chart illustrating one embodiment of a method for evaluating homeostatic capacity of a subject, specifically showing a machine learning algorithm used in classification.

FIG. 2 illustrates aspects of the device of FIG. 1 in greater detail, including implementation of a machine learning algorithm in order to classify subjects according to their homeostatic capacities. Biometric data comprising a training set 210 is obtained from a database 200, which contains classified or labeled, training examples with biometric values. In other words, database 200 has biometric data from individuals of known homeostatic capacities. The training set biometric data 210 is input into a machine learning algorithm 250 of a homeostatic capacity evaluation module 240. A user 220 may define the type of classification/machine learning algorithm 230 to be used. The machine learning algorithm 250 is optimized using one of a variety of statistical means known in the art, such as cross-validation. Alternatively (not shown), the user may define a plurality of machine learning algorithms, or the computer may define a plurality of machine learning algorithms, for which optimization methods will be performed and the best (most accurate) will be used. Once the machine learning algorithm 250 is optimized, a classification rule 260 is established. Dynamic biometric obtainment module 270 is adapted to obtain subject's dynamic biometric data 280. This biometric data 280 from the subject is then input into the classification rule 260 of the homeostatic capacity evaluation module 240. The subject's homeostatic capacity is evaluated using the classification rule 260. The predicted homeostatic capacity classification/evaluation is provided to the user by the homeostatic capacity evaluation output module 290.

As would be recognized by one of skilled in the art, many different software, firmware, hardware options and data structures can be employed in devices of the invention, e.g., as described above. In some instances, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the datafiles and the programming can be exported to a cloud computer, which runs the program, and returns an output to the user.

The memory of a computer system can be any device that can store information for retrieval by a processor, and can include magnetic or optical devices, or solid-state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable. Operation of the computer is controlled primarily by operating system, which is executed by a central processing unit. The operating system can be stored in a system memory. In some embodiments, the operating system includes a file system. In addition to the operating system, one possible implementation of the system memory includes a variety programming files and data files for implementing the method described above.

Where desired, the devices may include one or more sensors, e.g., configured to obtain biometric data, e.g., as described above. In certain aspects, a sensor includes one or more, such as a set of two or more, such as two or three, electrodes that provide for sensing. For example, the electrodes may be configured to generate electrocardiogram data. Alternatively, physiological sensors distinct from electrodes may be included in the device. For example, a temperature sensor, such as a thermistor, CMOS temperature sensor, resistive temperature devices (RTDs), may be employed to obtain precise measurements of temperature. An additional physiological sensor may include an LED and a photodiode combined into a pulse oximeter, which may be employed to measure blood oxygenation, which would also give information about pulse pressure. The device may also include analyte detection sensors. For example, specific chemical sensors may be incorporated into the devices to detect the presence of various agents, e.g., alcohol, glucose, BNP (B-type Natriuretic peptide, which is associated with cardiac disease), etc. Sensors of interest include those configured to detect the presence of a chemical analyte in a biological fluid sample, where analytes of interest include, but are not limited to: blood sugar (glucose), cholesterol, bilirubin, creatine, various metabolic enzymes, hemoglobin, heparin, hematocrit, vitamin K or other clotting factors, uric acid, carcinoembryonic antigen or other tumor antigens, various reproductive hormones such as those associated with ovulation or pregnancy, drugs of abuse and/or metabolites thereof; blood alcohol concentration, etc. In certain aspects, substances or properties for which the receiver is configured to detect include lactate (important for athletes), oxygen, pH, alcohol, tobacco metabolites, and illegal drugs (important for both medical diagnosis and law enforcement). Where the devices includes an analyte detecting sensing element, this sensing element can be configured in the receiver in a number of different ways. For example, a sensor that includes a selectively permeable membrane which is permeable to the agent one wants to detect may be provided, where there is an isolated cell behind the membrane and the agent passes through the membrane. Changes in the properties, such as electrical properties, of the cell, are then measured. In certain aspects, a small reservoir on the side of the devices with a membrane across it is employed, and electrical circuitry behind it is measured. Also of interest are ChemFET sensors, which are based on the binding of analyte to the sensor causing a change in the conductivity. In certain aspects, a material whose electrical properties (or other properties) are changed when the material, e.g., protein analyte, binds to it are employed. Blood alcohol concentration may be determined any number of ways, including but not limited to: sensors that analyze fluid samples, such as perspiration, optical spectroscopic sensors, etc.

Of interest are receivers that include at least an electrocardiography (ECG) sensor module. An ECG sensor module is a module which is configured to obtain ECG data and, if desired, additionally perform one or more of processing the data in some way, storing the data and retransmitting the data. The ECG data may be employed by the receiver to derive a number of different metrics, including but not limited to: R-wave, heart rate, heart rate variability, respiration rate, etc. Where the device includes one or more physiological sensing functionalities, the device may further include sensing modules that are configured to obtain and process data from these sensing functionalities. For example, where the device includes an ECG sensing functionality, the device may include an appropriate functional module (for example in the form of programming) that can handle and process the raw data from these sensors.

In use, dynamic biometric data information is input into the system, and a user receives a homeostatic capacity evaluation from the system, e.g., as described above. In certain embodiments, instructions in accordance with the method (e.g., in the form of a mobile app or other type of structure) described herein can be coded onto a computer-readable medium in the form of "programming", where the term "computer readable medium" as used herein refers to any storage or transmission medium (including non-transitory version so such) that participates in providing instructions and/or data to a computer for execution and/or processing. Programming may take the form of any convenient algorithms. In some instances, programming may include statistical analysis. Any of a variety of statistical methods known in the art and described herein, can be used, where statistical methods of interest include, for example, discriminant analysis, classification analysis, cluster analysis, analysis of variance (ANOVA), regression analysis, regression trees, decision trees, nearest neighbor algorithms, principal components, factor analysis, ensemble learning, AdaBoost, ALOPEX, analogical modeling, cascading classifiers, case-based reasoning, classifier chains, co-training, information fuzzy networks, logic learning machine, perceptron, multi-dimensional scaling and other methods of dimensionality reduction, likelihood models, hypothesis testing, kernel density estimation and other smoothing techniques, cross-validation and other methods to guard against overfitting of the data, the bootstrap and other statistical resampling techniques, artificial intelligence, including artificial neural networks, machine learning, data mining, and boosting algorithms, and Bayesian analysis, etc.

Examples of storage media include a floppy disk, hard disk, optical disk, magneto-optical disk, CD-ROM, CD-ft magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer. The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

As mentioned above, the functional modules may be performed by a variety of different hardware, firmware and software configurations. In some instances, the functional modules will be distributed among a system of two or more distinct devices, e.g., mobile devices, remote devices (such as cloud server devices), laboratory instrument devices, etc., which may be in communication with each other, e.g., via wired or wireless communication. In other instances, the distinct functional modules will be integrated into a single device. Where the distinct functional modules are integrated into a single device, the device may have a variety of configurations. For example, the device may be a laboratory device, which may or may not be configured to a bench top device. In yet other instances, the device may be a handheld device, e.g., a smartphone or tablet type device. In yet other instances, the device may be a wearable device, such as a watch type device, a wearable patch type device, etc.

Embodiments of the invention may employ virtual reality components and virtual reality mediated protocols. Virtual reality (both display and input devices) or other such simulators may be employed. Virtual reality and similar simulators may be employed to collect data (e.g., through the use of various biometric sensors that work in conjunction with virtual reality systems, such as measuring heart rate, eye movements and blink rates, measuring electrical impulses on the head (e.g., ear, neck, etc.), brain waves, etc.). Virtual reality and similar simulators may be employed to apply various stimuli (e.g., create a psychological/physiological condition such as fear of heights, etc., and the attendant increases in blood pressure, psychological distress, etc.). Virtual reality and similar simulators may be employed to in therapeutic embodiments, for example, to induce physiological, chemical, electrical, behavioral, and or psychological change—e.g., to overcome phobias, to reduce blood pressure/treat hypertension (e.g., via paradoxically elevating pressure), treat depression, improve mood and well-being, improve system balance or ability to restore balance, etc. In such instances, any convenient virtual reality input devices or similar simulators, incorporating one or more of the senses, may be employed, e.g., to improve homeostatic capacity at all system levels. Suitable virtual reality systems include consumer use at home, at retail locations (as a service), or medical grade, e.g., that are configured to be used in clinic settings or at home. Where desired, the virtual reality systems may be connected to other devices, such an exercise machine with various biometric monitors to collect data, apply stimuli and be used for therapy. These could be used for any number of medical indications, performance enhancement for athletes, general consumer wellness use, etc.

In addition, the present invention contemplates the storage and access to information present thereon, e.g., concerning homeostatic capacity evaluation, treatment regimen, therapeutic administration, etc., where such access may be public or via an appropriate secured and private setting, e.g., wherein HIPAA standards are followed, such that the system may be HIPAA compliant.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of treating a subject for a condition, the method comprising:
   applying a stimulus to and withdrawing the stimulus from the subject;
   obtaining a panel of dynamic measures of homeostatic capacity for the subject during the application of the stimulus and after withdrawing the stimulus by obtaining dynamic biometric data from different biological systems of the subject;
   evaluating the panel of dynamic measures of homeostatic capacity of the subject based on age-based normative values for said measures of homeostatic capacity; and
   administering a therapy to the subject in a manner sufficient to modulate the panel of the subject's different dynamic measures of homeostatic capacity to more closely approximate target dynamic measures of homeostatic capacity and treat the subject for the condition.

2. The method according to claim 1, wherein the dynamic biometric data comprises biometric data obtained over a period of time.

3. The method according to claim 2, wherein the biometric data is continuously obtained over the period of time.

4. The method according to claim 1, wherein the dynamic biometric data is obtained by evaluating a biometric parameter for a rate of change over a period of time.

5. The method according to claim 1, wherein the method comprises physically monitoring the subject to obtain the dynamic biometric data.

6. The method according to claim 1, wherein the method comprises analyzing a sample from the subject to obtain the dynamic biometric data.

7. The method according to claim 1, wherein the therapy comprises a traditional medical therapy.

8. The method according to claim 1, wherein the condition is a disease condition.

9. The method according to claim 8, wherein the disease condition is an aging-associated disease condition.

10. The method according to claim 1, wherein the condition is aging.

11. The method according to claim 1, wherein the subject is a mammal.

12. The method according to claim 11, wherein the subject is a primate.

13. The method according to claim 12, wherein the subject is a human.

14. The method according to claim 11, wherein the subject is a laboratory research animal.

15. The method according to claim 1, wherein the panel of dynamic measures of homeostatic capacity comprises two or more of baroreceptor sensitivity, heart rate variability, flow-mediated vasodilation, postprandial glucose and triglyceride tolerance tests, gait balance, pupillary light reflex, and recovery time after cardiac stress.

16. The method according to claim 1, wherein the stimulus is a physical stimulus comprising a change in orientation of the subject, exercise, a change in temperature experienced by the subject, or a combination thereof.

* * * * *